(12) United States Patent
Hubschwerlen et al.

(10) Patent No.: US 7,820,655 B2
(45) Date of Patent: Oct. 26, 2010

(54) ETHANOL OR 1,2-ETHANEDIOL CYCLOHEXYL ANTIBIOTIC DERIVATIVES

(75) Inventors: Christian Hubschwerlen, Durmenach (FR); Jean-Philippe Surivet, Kembs (FR); Cornelia Zumbrunn Acklin, Basel (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 245 days.

(21) Appl. No.: 12/279,329

(22) PCT Filed: Feb. 14, 2007

(86) PCT No.: PCT/IB2007/050482

§ 371 (c)(1),
(2), (4) Date: Aug. 13, 2008

(87) PCT Pub. No.: WO2007/093963

PCT Pub. Date: Aug. 23, 2007

(65) Prior Publication Data

US 2009/0005368 A1  Jan. 1, 2009

(30) Foreign Application Priority Data

Feb. 15, 2006 (WO) ............... PCT/IB2006/050505

(51) Int. Cl.
C07D 498/04 (2006.01)
A61K 31/542 (2006.01)
A61K 31/5383 (2006.01)
(52) U.S. Cl. ............. 514/230.5; 544/48; 544/105; 514/224.2
(58) Field of Classification Search .............. 544/48, 544/105; 514/224.2, 230.5
See application file for complete search history.

(56) References Cited

U.S. PATENT DOCUMENTS 3,979,387 A  9/1976  Dreikorn et al.

FOREIGN PATENT DOCUMENTS

| WO | WO 00/21948 | 4/2000 |
|---|---|---|
| WO | WO 03/087098 | 10/2003 |
| WO | WO 2004/002992 | 1/2004 |
| WO | WO 2004/058144 | 7/2004 |
| WO | WO 2004/089947 | 10/2004 |
| WO | WO 2006/032466 | 3/2006 |

OTHER PUBLICATIONS

Int J. Pharm. (1 986), 33, 201-217.
Remington, *The Science and Practice of Pharmacy*, 21st Edition (2005).
G. Benz in *Comprehensive Organic Synthesis*, B.M. Trost, I. Fleming, Eds; Pergamon Press: New York (1991), vol. 6, p. 381.
Synleff (1 996), 521.
O. Mitsunobu, *Synthesis* (1981), 1.
*Tetrahedron Lett.* (1981), 22, 1287.
*J. Org. Chem.* (1963), 28, 1140.
R.O. and M.K. Hutchins, *Comprehensive Organic Synthesis, B.M. Trost, I. Fleming, Eds; Pergamon Press: New York* (1991), vol. 8, p. 25-78.
P.J. Kocienski, *'Protecting Groups'*, Thieme (1994).
Sonogashira, K. in *Metal-Catalyzed Reactions, Diedrich, F., Stang, P.J., Eds; Wiley- VCH: New York* (1998).
*Chem. Rev.* (1994), 94,2483.
Blakemore, P.R in *J. Chem. Soc., Perkin Trans. I* (2002), 2563-2585.
*J. Org. Chem.* (1990), 55, 1857.
*J. Am. Chem. Soc.* (1 987), 109,5478.
J.T. Adams, *J. Am. Chem. Soc.* (1946), 68, 1317.
T.A. Williamson in *Heterocyclic Compounds* (1957), 6, 324.
Y. Abe et al. in *J. Med. Chem.* (1998), 41, 4062.
*J. Org. Chem.* (1980), 45,1514.
*Synth. Commun.* (1981), 11, 513.
*Org. Lett.* (2002), 4,4399-4401.
Cha, J.K. *Chem. Rev.* (1995), 95, 1761-1795.
*J. Org. Chem.* (2005), 70, 1508-1510.
*J. Am. Chem. Soc.* (1 946), 68, 1301 -1 303.
*Synthesis* (1981), 165.
*J. Am. Chem. Soc.* (1991), 113,7277.
*Tetrahedron Lett.* (1972), 3769.
*Synth. Commun.* (1989). 19, 561.
*Synlett* (2003), 59.
Wikler, et al. "Methods for Dilution Antimicrobial Suseptibility Tests for Bacteria That Grow Aerobically", Approved Standard—.Seventh Edition, vol. 26, No. 2, Clinical and Laboratory Standards Institute, (2006).

*Primary Examiner*—Kahsay T Habte
(74) *Attorney, Agent, or Firm*—Hunton & Williams LLP

(57) ABSTRACT

The invention relates to antibiotic ethanol or 1,2-ethanediol cyclohexyl derivatives of formula (I) wherein R1 represents $(C_1-C_4)$alkoxy; one or two of U, V, W and X represents) N and the remaining represent each independently CH or, in the case of V or X, may also represent $CR^a$; $R^a$ represents halogen; $R^2$ represents H or OH; A represents $CH_2$, CO, $CH_2CH=CH$ or $COCH=CH$; D represents a phenyl group optionally substituted one or two times by halogen atoms, or D represents a group of the formula (II) in which Q is oxygen or sulphur; and to salts of these derivatives of formula (I).

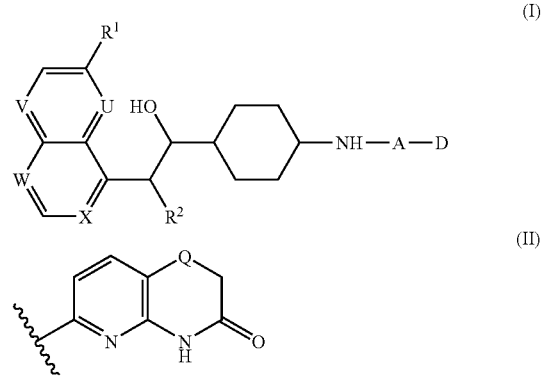

15 Claims, No Drawings

ETHANOL OR 1,2-ETHANEDIOL CYCLOHEXYL ANTIBIOTIC DERIVATIVES

CONTINUITY DATA

This application is a national stage of PCT/IB2007/050482, filed on Feb. 14, 2007, which in turn claims priority to PCT/IB2006/050505, filed on Feb. 15, 2006. Both applications to which priority is claimed are incorporated in their entirety by reference.

FIELD OF INVENTION

The present invention concerns novel antibiotics, a pharmaceutical antibacterial composition containing them and the use of these compounds in the manufacture of a medicament for the treatment of infections (e.g. bacterial infections). These compounds are useful antimicrobial agents effective against a variety of human and veterinary pathogens including among others Gram positive and Gram negative aerobic and anaerobic bacteria and mycobacteria.

BACKGROUND OF INVENTION

The intensive use of antibiotics has exerted a selective evolutionary pressure on micro-organisms to produce genetically based resistance mechanisms. Modern medicine and socio-economic behaviour exacerbates the problem of resistance development by creating slow growth situations for pathogenic microbes, e.g. in artificial joints, and by supporting long-term host reservoirs, e.g. in immuno-compromised patients.

In hospital settings, an increasing number of strains of *Staphylococcus aureus, Streptococcus pneumoniae, Enterococcus* spp., and *Pseudomonas aeruginosa*, major sources of infections, are becoming multi-drug resistant and therefore difficult if not impossible to treat:

- *S. aureus* is resistant to β-lactam and quinolone antibiotics and now even to vancomycin;
- *S. pneumoniae* is becoming resistant to penicillin and quinolone antibiotics and even to new macrolides;
- Enteroccocci are quinolone and vancomycin resistant and β-lactam antibiotics are inefficacious against these strains;
- Enterobacteriacea are cephalosporin and quinolone resistant;
- *P. aeruginosa* are β-lactam and quinolone resistant.

Further new emerging organisms like *Acinetobacter* spp., which have been selected during therapy with the currently used antibiotics, are becoming a real problem in hospital settings.

In addition, microorganisms that are causing persistent infections are increasingly being recognized as causative agents or cofactors of severe chronic diseases like peptic ulcers or heart diseases.

WO 03/087098 discloses, among others, compounds of the general formula (A1)

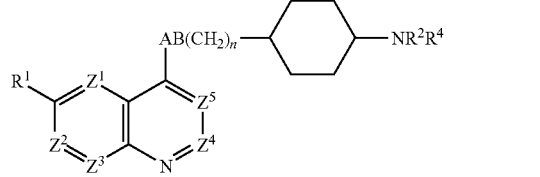

wherein
one of $Z^1$, $Z^2$, $Z^3$, $Z^4$ and $Z^5$ is N, one is $CR^{1a}$ and the remainder are CH, or one of $Z^1$, $Z^2$, $Z^3$, $Z^4$ and $Z^5$ is $CR^{1a}$ and the remainder are CH;
$R^1$ and $R^{1a}$ can notably be independently selected from hydrogen, halogen and $C_1$-$C_6$ alkoxy, provided that when $Z^1$, $Z^2$, $Z^3$, $Z^4$ and $Z^5$ are $CR^{1a}$ or CH, then $R^1$ is not hydrogen;
n is 0 or 1 and AB can notably represent a $CR^6R^7$—$CR^8R^9$ radical wherein each of $R^6$, $R^7$, $R^8$ and $R^9$ is independently selected from. H; $(C_{1\text{-}6})$alkoxy; $(C_{1\text{-}6})$alkylthio; halo; trifluoromethyl; azido; $(C_{1\text{-}6})$alkyl; $(C_{2\text{-}6})$alkenyl; $(C_{1\text{-}6})$alkoxycarbonyl; $(C_{1\text{-}6})$alkylcarbonyl; $(C_{2\text{-}6})$alkenyloxycarbonyl; $(C_{2\text{-}6})$alkenylcarbonyl; hydroxy, amino or aminocarbonyl which may be substituted; $(C_{2\text{-}6})$alkenylsulphonyl; or $(C_{1\text{-}6})$aminosulphonyl wherein the amino group is optionally substituted by $(C_{1\text{-}6})$ alkyl or $(C_{2\text{-}6})$ alkenyl; or $R^6$ and $R^8$ together represent a bond and $R^7$ and $R^9$ are as above defined;
$R^2$ can be hydrogen, and
$R^4$ can be a group —U—$R^5_2$ in which $R^5_2$ is an optionally substituted bicyclic carbocyclic or heterocyclic ring system (A)

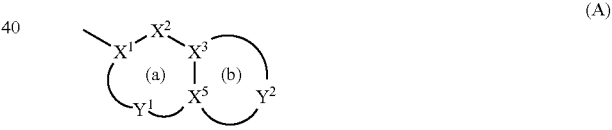

containing up to four heteroatoms in each ring in which at least one of rings (a) and (b) is aromatic,
$X^1$ is C or N when part of an aromatic ring or $CR^{14}$ when part of a non aromatic ring;
$X^2$ is N, $NR^{13}$, O, $S(O)_x$, CO or $CR^{14}$ when part of an aromatic or non-aromatic ring or may in addition be $CR^{14}R^{15}$ when part of a non aromatic ring;
$X^3$ and $X^5$ are independently N or C;
$Y^1$ is a 0 to 4 atom linker group each atom of which is independently selected from N, $NR^{13}$, O, $S(O)_x$, CO and $CR^{14}$ when part of an aromatic or non-aromatic ring or may additionally be $CR^{14}R^{15}$ when part of a non aromatic ring,
$Y^2$ is a 2 to 6 atom linker group, each atom of $Y^2$ being independently selected from N, $NR^{13}$, 0, $S(O)_x$, CO and $CR^{14}$ when part of an aromatic or non-aromatic ring or may additionally be $CR^{14}R^{15}$ when part of a non aromatic ring;
each $R^{13}$ can notably be hydrogen;
each of $R^{14}$ and $R^{15}$ can notably be hydrogen;
each x is independently 0, 1 or 2;
U is CO, $SO_2$ or $CH_2$; or
$R^4$ can also be a group —$X^{1a}$—$X^{2a}$—$X^{3a}$—$X^{4a}$ wherein the group $X^{1a}$—$X^{2a}$—$X^{3a}$ can notably be $CH_2CH$=CH or COCH=CH and $X^{4a}$ can notably be a phenyl substituted one to three times wherein the substituents are notably selected from halogen atoms;

which compounds of formula (A1) can be used as antibacterials.

WO 2004/002992 discloses, among others, compounds of the general formula (A2)

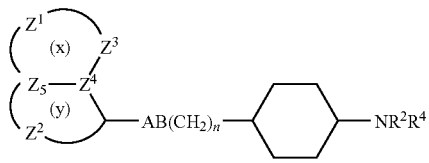

wherein both rings (x) and (y) can be aromatic, $Z^1$ can be a 3 atom linker group each atom of which can be independently selected from N and CH, $Z^2$ can be a 3 atom linker group each atom of which can be independently selected from N and CH, $Z^3$ can be CH, $Z^4$ and $Z^5$ can both be carbon atoms, n is 0 or 1 and AB represents notably a $CR^6R^7$—$CR^8R^9$ radical wherein each of $R^6$, $R^7$, $R^8$ and $R^9$ is independently selected from. H; $(C_{1-6})$alkoxy; $(C_{1-6})$alkylthio; halo; trifluoromethyl; azido; $(C_{1-6})$alkyl; $(C_{2-6})$alkenyl; $(C_{1-6})$alkoxycarbonyl; $(C_{1-6})$alkylcarbonyl; $(C_{2-6})$alkenyloxycarbonyl; $(C_{2-6})$alkenylcarbonyl; hydroxy, amino or aminocarbonyl which may be substituted; $(C_{2-6})$alkenylsulphonyl; or $(C_{1-6})$aminosulphonyl wherein the amino group is optionally substituted by $(C_{1-6})$ alkyl or $(C_{2-6})$ alkenyl; or $R^6$ and $R^8$ together represent a bond and $R^7$ and $R^9$ are as above defined;

$R^2$ can be hydrogen, and $R^4$ can be a group —U—$R^5_2$ wherein U can be $CH_2$ and $R^5_2$ is an optionally substituted bicyclic carbocyclic or heterocyclic ring system (A)

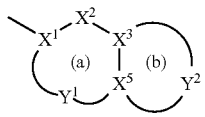

containing up to four heteroatoms in each ring in which at least one of rings (a) and (b) is aromatic, $X^1$ is C or N when part of an aromatic ring or $CR^{14}$ when part of a non aromatic ring;

$X^2$ is N, $NR^{13}$, O, $S(O)_x$, CO or $CR^{14}$ when part of an aromatic or non-aromatic ring or may in addition be $CR^{14}R^{15}$ when part of a non aromatic ring;

$X^2$ is N, $NR^{13}$, O, $S(O)_x$, CO or $CR^{14}$ when part of an aromatic or non-aromatic ring or may in addition be $CR^{14}R^{15}$ when part of a non aromatic ring;

$Y^1$ is a 0 to 4 atom linker group each atom of which is independently selected from N, $NR^{13}$, O, $S(O)_x$, CO and $CR^{14}$ when part of an aromatic or non-aromatic ring or may additionally be $CR^{14}R^{15}$ when part of a non aromatic ring, $Y^2$ is a 2 to 6 atom linker group, each atom of $Y^2$ being independently selected from N, $NR^{13}$, O, $S(O)_x$, CO and $CR^{14}$ when part of an aromatic or non-aromatic ring or may additionally be $CR^{14}R^{15}$ when part of a non aromatic ring;

each $R^{13}$ can notably be hydrogen;

each of $R^{14}$ and $R^{15}$ can notably be hydrogen;

each x is independently 0, 1 or 2;

U is CO, $SO_2$ or $CH_2$;

$R^4$ can also be a group —$X^{1a}$—$X^{2a}$—$X^{3a}$—$X^{4a}$ wherein the group $X^{1a}$—$X^{2a}$—$X^{3a}$ can notably be $CH_2CH$=CH or COCH=CH and $X^{4a}$ can notably be a phenyl substituted one to three times wherein the substituents are notably selected from halogen atoms;

which compounds of formula (A2) can be used as antibacterials.

It should however be noted that no specific example of compound of formula I as defined in this application is taught in WO 03/087098 or WO 2004/002992.

Besides, PCT application No. PCT/EP2005/010154 (published as WO 2006/032466 after the priority date of this application) discloses antibacterial compounds that are structurally similar to those of the instant invention, except the fact that they do not contain a cyclohexane-1,4-diyl motif but a cyclohexane-1,3-diyl, a tetrahydropyrane-2,5-diyl or a piperidine-2,5-diyl motif instead.

SUMMARY OF INVENTION

It has now surprisingly been found that certain ethanol or 1,2-ethanediol cyclohexyl derivatives are especially potent antimicrobial agents that are notably effective against a variety of multi-drug resistant bacteria. Thus, the present invention relates to ethanol or 1,2-ethanediol cyclohexyl derivatives of the formula I

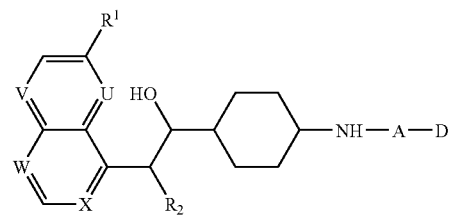

wherein $R^1$ represents $(C_1-C_4)$alkoxy;

one or two of U, V, W and X represent(s) N and the remaining represent each independently CH or, in the case of V or X, may also represent $CR^a$;

$R^a$ represents halogen;

$R^2$ represents H or OH;

A represents $CH_2$, CO, $CH_2CH$=CH or COCH=CH;

D represents a phenyl group optionally substituted one or two times by halogen atoms, or D represents a group of the formula

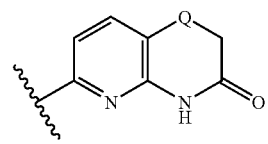

in which Q is oxygen or sulphur;

and to salts of compounds of formula I.

The following paragraphs provide definitions of the various chemical moieties for the compounds according to the invention and are intended to apply uniformly throughout the specification and claims, unless an otherwise expressly set out definition provides a broader or narrower definition:

The term "alkoxy", used alone or in combination, refers to a saturated straight or branched chain alkoxy group, containing from one to ten, preferably one to six, and in particular one to four carbon atoms. Representative examples of alkoxy groups include, but are not limited to, methoxy, ethoxy, propoxy, iso-propoxy, n-butoxy, iso-butoxy, sec-butoxy, tert-butoxy or n-hexyloxy. The term "($C_1$-$C_x$)alkoxy" refers to a straight or branched chain alkoxy group containing 1 to x carbon atoms.

The term "halogen" refers to fluorine, chlorine, bromine or iodine, preferably to fluorine or chlorine.

When in the formula

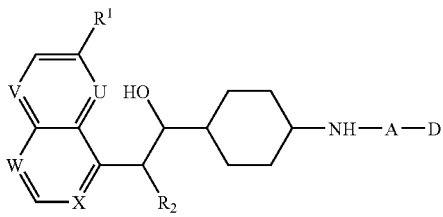

A represents the radical COCH=CH, this means specifically that the CO part of the COCH=CH radical is attached to the nitrogen and that the =CH part of the COCH=CH radical is attached to the D group. This is applicable mutatis mutandis to all radicals that make the A radical. In other words, the left part of a radical is always attached to the right part of the radical that is next to the left.

Besides, the term "room temperature" as used herein refers to a temperature of 20° C.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

In particular, the invention relates to compounds of formula I that are also compounds of formula $I_{CE}$

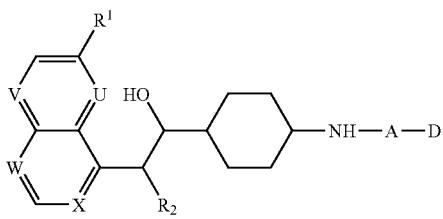

$I_{CE}$ wherein
$R^1$ represents $C_1$-$C_4$ alkoxy (and preferably methoxy);
one or two of U, V and W represent(s) N and the remaining represent each independently CH or, in the case of V, may also represent $CR^a$;

X represents CH or $CR^a$;
$R^a$ represents halogen (and preferably fluorine);
$R^2$ represents H or OH;
A represents $CH_2$, CO, $CH_2CH$=CH or COCH=CH;
D represents a phenyl group optionally substituted one or two times by halogen atoms, or D represents a group of the formula:

in which Q is oxygen or sulphur;
and to salts of compounds of formula $I_{CE}$.

Preferred compounds of formula $I_{CE}$ are those wherein at least one of the following characteristics is present:
$R^1$ represents methoxy;
one or two of U, V and W represent(s) N and the remaining represent each independently CH or, in the case of V, may also represent $CR^a$, X represents CH or $CR^a$ and $R^a$ represents fluorine;
A represents $CH_2CH$=CH or COCH=CH and D represents a phenyl group optionally substituted one or two times by fluorine atoms, or A represents $CH_2$ or CO and D represents a group of the formula

in which Q is oxygen or sulphur.

Particularly preferred compounds of formula $I_{CE}$ will be those wherein D represents 2,5-difluorophenyl, 3-fluorophenyl or the heteroaryl group

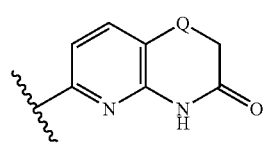

in which Q is oxygen or sulphur.

Preferred compounds of formula I are those wherein at least one of the following characteristics is present:
$R^1$ represents ($C_1$-$C_3$)alkoxy;
one or two of U, V, W and X represent(s) N, and the remaining represent each independently CH or, in the case of V or X, may also represent $CR^a$, $R^a$ representing fluorine;
A represents $CH_2CH$=CH or COCH=CH and D represents a phenyl group optionally substituted one or two times by fluorine atoms, or
or A represents $CH_2$ or CO and D represents a group of the formula

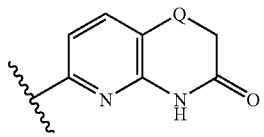

in which Q is oxygen or sulphur.

More preferred compounds of formula I are those wherein at least one of the following further characteristics is present:

$R^1$ represents $(C_1-C_2)$alkoxy;

one or two of U, V and W represent(s) N and the remaining represent each independently CH or, in the case of V, may also represent $CR^a$, X represents CH or $CR^a$ and $R^a$ represents fluorine;

A represents $CH_2CH=CH$ and D represents a phenyl group optionally substituted one or two times by fluorine atoms, or A represents $CH_2$ and D represents a group of the formula

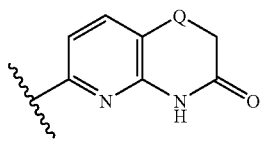

in which Q is oxygen or sulphur.

Particularly preferred compounds of formula I are those wherein at least one of the following further characteristics is present:

$R^1$ represents methoxy;

one or two of U, V and W represent(s) N and the remaining represent each independently CH or, in the case of V, may also represent $CR^a$, X represents CH or $CR^a$ and $R^a$ represents fluorine;

A represents $CH_2CH=CH$ and D represents a phenyl group substituted two times by fluorine atoms (especially 2,5-difluorophenyl), or A represents $CH_2$ and D represents a group of the formula

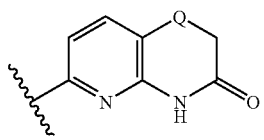

in which Q is oxygen or sulphur.

Preferred combinations for the symbols U, V, W and X in the compounds of formula I or $I_{CE}$ are evident from the following particular structures:

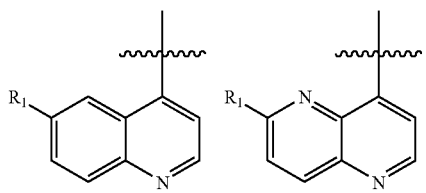

-continued

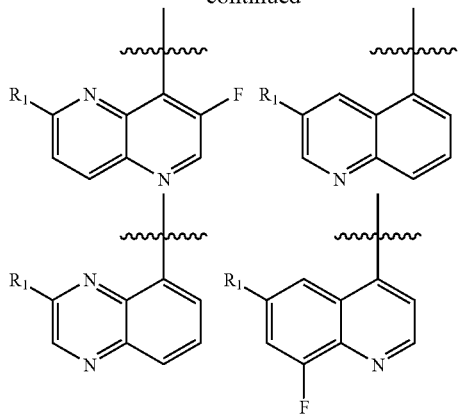

wherein $R^1$ is as defined in formula I above, and preferably $(C_1-C_3)$alkoxy (in particular $(C_1-C_2)$alkoxy and notably methoxy).

Thus, according to a first preferred embodiment of the invention, the compounds of formula I or $I_{CE}$ will be such that W represents N and each of U, V and X represents CH. According to a second preferred embodiment of the invention, the compounds of formula I or $I_{CE}$ will be such that each of U and W represents N and each of V and X represents CH. According to a third preferred embodiment of the invention, the compounds of formula I or $I_{CE}$ will be such that each of U and W represents N, V represents CH and X represents CF. According to a fourth preferred embodiment of the invention, the compounds of formula I or $I_{CE}$ will be such that V represents N and each of U, W and X represents CH. According to a fifth preferred embodiment of the invention, the compounds of formula I or $I_{CE}$ will be such that each of U and V represents N and each of W and X represents CH. According to a sixth preferred embodiment of the invention, the compounds of formula I or $I_{CE}$ will be such that W represents N, V represents CF and each of U and X represents CH.

Particularly preferred combinations for the symbols U, V, W and X in the compounds of formula I or $I_{CE}$ are evident from the following particular structures:

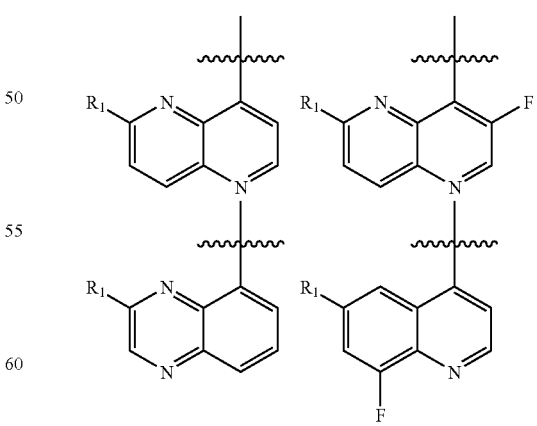

wherein $R^1$ is as defined in formula I above, and preferably $(C_1-C_3)$alkoxy (in particular $(C_1-C_2)$alkoxy and notably methoxy).

Particularly preferred meanings for D in the compounds of formula I are 2,5-difluorophenyl, 3-fluorophenyl, 3-oxo-3,4-dihydro-2H-pyrido[3,2-b][1,4]oxazin-6-yl and 3-oxo-3,4-dihydro-2H-pyrido[3,2-b][1,4]thiazin-6-yl.

Especially preferred are compounds of formula I or of formula $I_{CE}$ wherein the two substituents in position –1,4 on the cyclohexyl ring are trans configured and wherein the stereochemistry of the carbon bearing the hydroxy group is as depicted in structure Ia (i.e. (R) when $R^2$ is OH and (S) when $R^2$ is H):

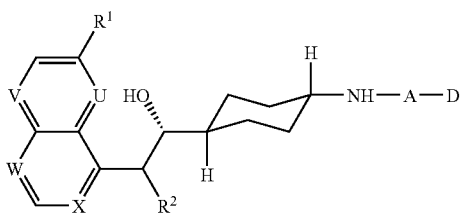

Ia

According to a first variant of this invention, the compounds of formula I will be such that D is a phenyl group optionally substituted one or two times by halogen atoms. The compounds according to this variant will be referred to hereafter as "compounds of formula $I_{ph}$".

Preferred compounds of formula $I_{Ph}$ are those wherein at least one of the following characteristics is present:
  $R^1$ represents $(C_1-C_3)$alkoxy;
  one or two of U, V, W and X represent(s) N and the remaining represent each independently CH or, in the case of V or X, may also represent $CR^a$, $R^a$ representing halogen;
  A represents $CH_2CH=CH$ or $COCH=CH$;
  D represents a phenyl group optionally substituted one or two times by fluorine atoms.

More preferred compounds of formula $I_{Ph}$ are those wherein at least one of the following characteristics is present:
  $R^1$ represents $(C_1-C_2)$alkoxy (and preferably methoxy);
  one or two of U, V and W represent(s) N and the remaining represent each independently CH or, in the case of V, may also represent $CR^a$, X represents CH or $CR^a$, $R^a$ representing fluorine;
  $A^2$ represents $CH_2CH=CH$;
  D represents phenyl, 3-fluorophenyl or 2,5-difluorophenyl (notably 3-fluorophenyl or 2,5-difluorophenyl, and in particular 2,5-difluorophenyl).

According to a second variant of this invention, the compounds of formula I will be such that D is a group of the formula

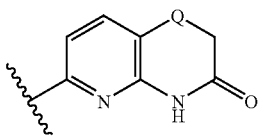

The compounds according to this variant will be referred to hereafter as "compounds of formula $I_{Het}$".

Preferred compounds of formula $I_{Het}$ are those wherein at least one of the following characteristics is present:
  $R^1$ represents $(C_1-C_3)$alkoxy;
  one or two of U, V, W and X represent(s) N and the remaining represent each independently CH or, in the case of V or X, may also represent $CR^a$, $R^a$ representing halogen;
  A represents $CH_2$ or CO.

More preferred compounds of formula $I_{Het}$ are those wherein at least one of the following characteristics is present:
  $R^1$ represents $(C_1-C_2)$alkoxy (and preferably methoxy);
  one or two of U, V and W represent(s) N and the remaining represent each independently CH or, in the case of V, may also represent $CR^a$, X represents CH or $CR^a$, $R^a$ representing fluorine;
  A represents $CH_2$.

Particularly preferred compounds of formula I are the following:
  6-({trans-4-[(1R)-1-hydroxy-2-(3-methoxy-quinolin-5-yl)-ethyl]-cyclohexylamino}-methyl)-4H-pyrido[3,2-b][1,4]thiazin-3-one;
  6-({trans-4-[(1S)-1-hydroxy-2-(3-methoxy-quinolin-5-yl)-ethyl]-cyclohexylamino}-methyl)-4H-pyrido[3,2-b][1,4]thiazin-3-one;
  3-oxo-3,4-dihydro-2H-pyrido[3,2-b][1,4]thiazine-6-carboxylic acid trans-{4-[(1R,2R)-1,2-dihydroxy-2-(6-methoxy-[1,5]naphthyridin-4-yl)-ethyl]-cyclohexyl}-amide;
  6-(trans-{4-[(1R,2R)-1,2-dihydroxy-2-(6-methoxy-[1,5]naphthyridin-4-yl)-ethyl]-cyclohexylamino}-methyl)-4H-pyrido[3,2-b][1,4]thiazin-3-one;
  3-oxo-3,4-dihydro-2H-pyrido[3,2-b][1,4]thiazine-6-carboxylic acid trans-{4-[(1S)-1-hydroxy-2-(6-methoxy-[1,5]naphthyridin-4-yl)-ethyl]-cyclohexyl}-amide;
  6-(trans-{4-[(1S)-1-hydroxy-2-(6-methoxy-[1,5]naphthyridin-4-yl)-ethyl]-cyclohexylamino}-methyl)-4H-pyrido[3,2-b][1,4]thiazin-3-one;
  6-({trans-4-[(1R,2R)-1,2-dihydroxy-2-(3-methoxy-quinoxalin-5-yl)-ethyl]-cyclohexylamino}-methyl)-4H-pyrido[3,2-b][1,4]thiazin-3-one;
  6-(trans-{4-[(1R,2R)-1,2-dihydroxy-2-(3-methoxy-quinoxalin-5-yl)-ethyl]-cyclohexylamino}-methyl)-4H-pyrido[3,2-b][1,4]oxazin-3-one;
  6-({trans-4-[(1S,2S)-1,2-dihydroxy-2-(3-methoxy-quinoxalin-5-yl)-ethyl]-cyclohexylamino}-methyl)-4H-pyrido[3,2-b][1,4]thiazin-3-one;
  6-(trans-{4-[(1S,2S)-1,2-dihydroxy-2-(3-methoxy-quinoxalin-5-yl)-ethyl]-cyclohexylamino}-methyl)-4H-pyrido[3,2-b][1,4]oxazin-3-one;
  (1R,2R)-1-{trans-4-[(E)-3-(2,5-difluoro-phenyl)-allylamino]-cyclohexyl}-2-(3-methoxy-quinoxalin-5-yl)-ethane-1,2-diol;
  6-(trans-{4-[(1R)-1-hydroxy-2-(6-methoxy-[1,5]naphthyridin-4-yl)-ethyl]-cyclohexylamino}-methyl)-4H-pyrido[3,2-b][1,4]thiazin-3-one;
  6-(trans {4-[1-(1R)-hydroxy-2-(6-methoxy-[1,5]naphthyridin-4-yl)-ethyl]-cyclohexylamino}-methyl)-4H-pyrido[3,2-b][1,4]oxazin-3-one;
  6-(trans-{4-[(1R,2R)-1,2-dihydroxy-2-(6-methoxy-quinolin-4-yl)-ethyl]-cyclohexylamino}-methyl)-4H-pyrido[3,2-b][1,4]thiazin-3-one;
  6-(trans-{4-[(1R,2R)-1,2-dihydroxy-2-(6-methoxy-quinolin-4-yl)-ethyl]-cyclohexylamino}-methyl)-4H-pyrido[3,2-b][1,4]oxazin-3-one;
  6-trans-({4-[(1R)-1-hydroxy-2-(6-methoxy-quinolin-4-yl)-ethyl]-cyclohexylamino}-methyl)-4H-pyrido[3,2-b][1,4]thiazin-3-one;
  6-trans-({4-[(1S)-1-hydroxy-2-(6-methoxy-quinolin-4-yl)-ethyl]-cyclohexylamino}-methyl)-4H-pyrido[3,2-b][1,4]thiazin-3-one;

(1R,2R)-1-{4-trans-[(E)-3-(2,5-difluoro-phenyl)-ally-lamino]-cyclohexyl}-2-(6-methoxy-[1,5]naphthyridin-4-yl)-ethane-1,2-diol;

(1R,2R)-1-{trans-4-[(E)-3-(2,5-difluoro-phenyl)-ally-lamino]-cyclohexyl}-2-(8-fluoro-6-methoxy-quinolin-4-yl)-ethane-1,2-diol;

(E)-3-(2,5-difluoro-phenyl)-N-{trans-4-[(1R,2R)-2-(8-fluoro-6-methoxy-quinolin-4-yl)-1,2-dihydroxy-ethyl]-cyclohexyl}-acrylamide;

6-({trans-4-[(1R,2R)-2-(8-fluoro-6-methoxy-quinolin-4-yl)-1,2-dihydroxy-ethyl]-cyclohexylamino}-methyl)-4H-pyrido[3,2-b][1,4]thiazin-3-one;

3-(2,5-difluoro-phenyl)-N-{4-[2-(3-fluoro-6-methoxy-[1,5]naphthyridin-4-yl)-1,2-dihydroxy-ethyl]-cyclohexyl}-acrylamide;

(1R,2R)-1-{trans-4-[(E)-3-(2,5-difluoro-phenyl)-ally-lamino]-cyclohexyl}-2-(3-fluoro-6-methoxy-[1,5]naph-thyridin-4-yl)-ethane-1,2-diol;

(1R,2R)-1-(3-fluoro-6-methoxy-[1,5]naphthyridin-4-yl)-2-{trans-4-[(E)-3-(3-fluorophenyl)-allylamino]-cyclo-hexyl}-ethane-1,2-diol;

and salts (in particular pharmaceutically acceptable salts) thereof.

Compounds of formula I are suitable for the use as chemotherapeutic active compounds in human and veterinary medicine and as substances for preserving inorganic and organic materials in particular all types of organic materials for example polymers, lubricants, paints, fibres, leather, paper and wood.

These compounds according to the invention are particularly active against bacteria and bacteria-like organisms. They are therefore particularly suitable in human and veterinary medicine for the prophylaxis and chemotherapy of local and systemic infections caused by these pathogens as well as disorders related to bacterial infections comprising pneumonia, otitis media, sinusitis, bronchitis, tonsillitis, and mastoiditis related to infection by *Streptococcus pneumoniae, Haemophilus influenzae, Moraxella catarrhalis, Staphylococcus aureus, Enterococcus faecalis, E. faecium, E. casseliflavus, S. epidermidis, S. haemolyticus,* or *Peptostreptococcus* spp.; pharyngitis, rheumatic fever, and glomerulonephritis related to infection by *Streptococcus pyogenes,* Groups C and G streptococci, *Corynebacterium diphtheriae,* or *Actinobacillus haemolyticum*; respiratory tract infections related to infection by *Mycoplasma pneumoniae, Legionella pneumophila, Streptococcus pneumoniae, Haemophilus influenzae,* or *Chlamydia pneumoniae*; blood and tissue infections, including endocarditis and osteomyelitis, caused by *S. aureus, S. haemolyticus, E. faecalis, E. faecium, E. durans,* including strains resistant to known antibacterials such as, but not limited to, beta-lactams, vancomycin, aminoglycosides, quinolones, chloramphenicol, tetracyclines and macrolides; uncomplicated skin and soft tissue infections and abscesses, and puerperal fever related to infection by *Staphylococcus aureus*, coagulase-negative staphylococci (i.e., *S. epidermidis, S. haemolyticus,* etc.), *Streptococcus pyogenes, Streptococcus agalactiae,* Streptococcal groups C-F (minute colony streptococci), viridans streptococci, *Corynebacterium minutissimum, Clostridium* spp., or *Bartonella henselae*; uncomplicated acute urinary tract infections related to infection by *Staphylococcus aureus,* coagulase-negative staphylococcal species, or *Enterococcus* spp.; urethritis and cervicitis; sexually transmitted diseases related to infection by *Chlamydia trachomatis, Haemophilus ducreyi, Treponema pallidum, Ureaplasma urealyticum,* or *Neisserria gonorrheae*; toxin diseases related to infection by *S. aureus* (food poisoning and toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae,* or *Listeria* spp.; disseminated *Mycobacterium avium* complex (MAC) disease related to infection by *Mycobacterium avium,* or *Mycobacterium intracellulare*; infections caused by *Mycobacterium tuberculosis, M. leprae, M. paratuberculosis, M. kansasii,* or *M. chelonei*; gastroenteritis related to infection by *Campylobacter jejuni*; intestinal protozoa related to infection by *Cryptosporidium* spp.; odontogenic infection related to infection by viridans streptococci; persistent cough related to infection by *Bordetella pertussis*; gas gangrene related to infection by *Clostridium perfringens* or *Bacteroides* spp.; and atherosclerosis or cardiovascular disease related to infection by *Helicobacter pylori* or *Chlamydia pneumoniae*.

Compounds of formula I according to the present invention are further useful for the preparation of a medicament for the treatment of infections that are mediated by bacteria such as *E. coli, Klebsiella pneumoniae* and other Enterobacteriaceae, *Acinetobacter* spp., *Stenothrophomonas maltophilia, Neisseria meningitidis, Bacillus cereus, Bacillus anthracis, Corynebacterium* spp., *Propionibacterium acnes* and bacteroide spp.

Compounds of formula I according to the present invention are further useful to treat protozoal infections caused by *Plasmodium malaria, Plasmodium falciparum, Toxoplasma gondii, Pneumocystis carinii, Trypanosoma brucei* and *Leishmania* spp.

The present list of pathogens is to be interpreted merely as examples and in no way as limiting.

One aspect of this invention therefore relates to the use of a compound of formula I according to this invention, or of a pharmaceutically acceptable salt thereof, for the manufacture of a medicament for the prevention or treatment of a bacterial infection.

As well as in humans, bacterial infections can also be treated using compounds of formula I (or pharmaceutically acceptable salts thereof) in other species like pigs, ruminants, horses, dogs, cats and poultry.

The present invention also relates to pharmacologically acceptable salts and to compositions and formulations of compounds of formula I.

Any reference to a compound of formula I is to be understood as referring also to the salts (and especially the pharmaceutically acceptable salts) of such compounds, as appropriate and expedient.

Examples of pharmacologically acceptable salts of sufficiently basic compounds of formula I are selected from the group consisting of salts of physiologically acceptable mineral acids like hydrochloric, hydrobromic, hydroiodic, sulfuric, sulfamic, nitric and phosphoric acid; or salts of organic acids like methanesulfonic, ethanedisulfonic, p-toluenesulfonic, lactic, acetic, trifluoroacetic, oxalic, benzoic, citric, succinic, fumaric, maleic, mandelic, cinnamic, pamoic, stearic, glutamic, aspartic and salicylic acid. Further, a sufficiently acidic compound of formula I may form alkali or earth alkaline metal salts, for example sodium, potassium, lithium, calcium or magnesium salts; ammonium salts; or organic base salts, for example methylamine, dimethylamine, trimethylamine, triethylamine, ethylenediamine, ethanolamine, choline hydroxide, meglumin, piperidine, morpholine, tris-(2-hydroxyethyl)amine, lysine or arginine salts. For other examples of pharmaceutically acceptable salts, reference can be made notably to "Salt selection for basic drugs", *Int. J. Pharm.* (1986), 33, 201-217.

A pharmaceutical composition according to the present invention contains at least one compound of formula I (or a pharmaceutically acceptable salt thereof) as the active agent and optionally carriers and/or diluents and/or adjuvants, and may also contain additional known antibiotics.

As mentioned above, therapeutically useful agents that contain compounds of formula I, their salts and formulations thereof are also comprised in the scope of the present invention. In general, compounds of formula I will be administered by using the known and acceptable modes known in the art, either alone or in combination with any other therapeutic agent. Such therapeutically useful agents can be administered by one of the following routes: oral, e.g. as tablets, dragee, coated tablets, pills, semisolids, soft or hard capsules, for example soft and hard gelatine capsules, aqueous or oily solutions, emulsions, suspensions or syrups, parenteral including intravenous, intramuscular and subcutaneous injection, e.g. as an injectable solution or suspension, rectal as suppositories, by inhalation or insufflation, e.g. as a powder formulation, as microcrystal or as a spray (e.g. liquid aerosol), transdermal, for example via an transdermal delivery system (TDS) such as a plaster containing the active ingredient, topical or intranasal. The substance of the present invention can also be used to impregnate or coated devices that are foreseen for implantation like catheters or artificial joints. The pharmaceutically useful agents may also contain additives for conservation, stabilisation, e.g. UV stabilizers, emulsifiers, sweetener, aromatisers, salts to change the osmotic pressure, buffers, coating additives and antioxidants.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of Formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Another aspect of the invention concerns a method for the prevention or the treatment of a bacterial infection in a patient comprising the administration to said patient of a pharmaceutically active amount of a derivative according to formula I or a pharmaceutically acceptable salt thereof.

Besides, any preferences indicated for the compounds of formula I (whether for the compounds themselves, salts thereof, compositions containing the compounds or salts thereof, uses of the compounds or salts thereof, etc.) apply mutatis mutandis to compounds of formula $I_{CE}$, compounds of formula $I_{Ph}$ and compounds of formula $I_{Het}$.

Moreover, the compounds of formula I may also be used for cleaning purposes, e.g. to remove pathogenic microbes and bacteria from surgical instruments or to make a room or an area aseptic. For such purposes, the compounds of formula I could be contained in a solution or in a spray formulation.

The compounds of formula I can be manufactured in accordance with the present invention using the procedures described hereafter.

DETAILED DESCRIPTION

Preparation of Compounds of Formula I

Abbreviations:

The following abbreviations are used throughout the specification and the examples:

AD-mix α 1,4-bis(dihydroquinine)phthalazine, $K_3Fe(CN)_6$, $K_2CO_3$ and $K_2OsO_4.2H_2O$
AD-mix β 1,4-bis(dihydroquinidine)phthalazine, $K_3Fe(CN)_6$, $K_2CO_3$ and $K_2OsO_4.2H_2O$
AIBN 2,2'-azabisisobutyronitrile
Alloc allyloxycarbonyl
aq. aqueous
Boc tert-butoxycarbonyl
Cbz benzyloxycarbonyl
DCC dicyclohexyl carbodiimide
1,2-DCE 1,2-dichloroethane
DCM dichloromethane
DEAD diethyl azo dicarboxylate
DIAD diisopropyl azo dicarboxylate
DIBAH diisobutylaluminium hydride
DIPEA N,N-diisopropylethylamine
1,2-DME 1,2-dimethoxyethane
DMAP 4-dimethylaminopyridine
DMF N,N-dimethylformamide
DMSO dimethylsulfoxide
EA ethyl acetate
EDC 1-(3-dimethylaminopropyl)-3-ethylcarbodiimide hydrochloride
ESI electron Spray Ionisation
Ether or $Et_2O$ diethyl ether
EtOH ethanol
h hour(s)
HATU O-(7-azabenzotriazol-1-yl)-N,N,N',N'-tetramethyluronium hexafluorophosphate
Hept heptane
Hex hexane
HMPT hexamethylphosphorous triamide
HOBT 1-hydroxybenzotriazole hydrate
HPLC high performance liquid chromatography
HV high vacuum conditions
KHMDS potassium hexamethyldisilazane
LiHMDS lithium hexamethyldisilazane
MCPBA meta-chloroperbenzoic acid
MeCN acetonitrile
MeOH methanol
min minute(s)
MS mass spectroscopy
MsCl methanesulfonyl chloride
NBS N-bromosuccinimide
n-BuLi n-butyl lithium
NMO 4-methylmorpholine-N-oxide
org. organic
OTf triflate
Pd/C palladium on charcoal
$PPh_3$ triphenylphosphine
quant. quantitative
rt room temperature
$SiO_2$ silica gel
TEA triethylamine
TFA trifluoroacetic acid
THF tetrahydrofuran
TsCl para-toluenesulfonyl chloride General Preparation Methods:

The compounds of formula I can be manufactured in accordance with the present invention by a) reacting a compound of the formula TI

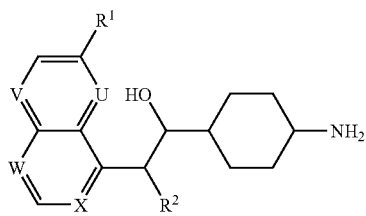

with a compound of the formula III

L⁰-A-D                                III wherein

R¹, R², U, V, W, X, A and D are as in formula I, and

L⁰ is appropriate to allow connection of the two moieties NH₂ and A-D of the compounds of formulae TI and III or b) transforming a compound of the formula IV:

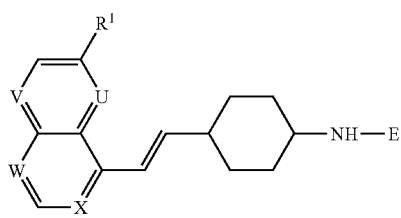

wherein

R¹, U, V, W and X are as in formula I, and

E is A-D (A and D being as defined in formula I) or a protecting group such as Cbz or Boc, into a compound of formula V

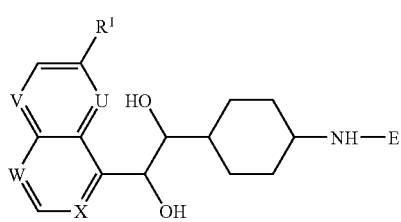

and, when E is a protecting group, removing the protecting group and reacting the deprotected intermediate with a compound of formula III

L⁰-A-D                                III wherein A and D are as in formula I and L⁰ is appropriate to allow connection of the two moieties NH₂ and A-D of said intermediate and the compound of formula III.

or c) transforming a compound of the formula VI

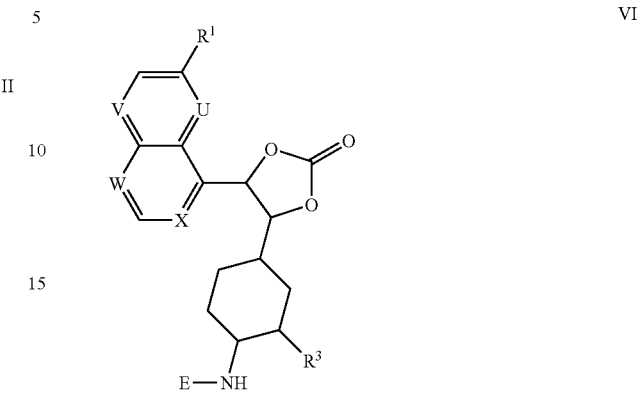

wherein E is A-D or a protecting group such as Boc and R¹, U, V, W, X, A and D are as in formula I, into a compound of formula I wherein R² is H, and, when E is a protecting group, removing the protecting group and reacting the deprotected intermediate with a compound of formula III

L⁰-A-D                                III wherein A and D are as in formula I and L⁰ is appropriate to allow connection of the two moieties NH₂ and A-D of said intermediate and the compound of formula III.

or d) reacting a compound of the formula VII

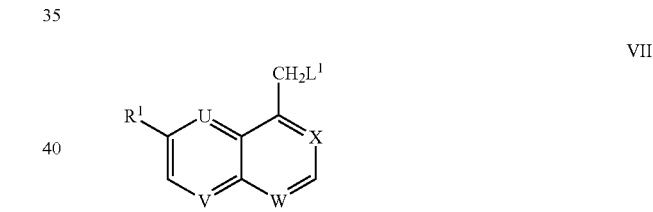

wherein R¹, U, V, W and X are as in formula I and L¹ is Mg-Hal (Hal being a halogen atom) or L¹, with a compound of formula VIII

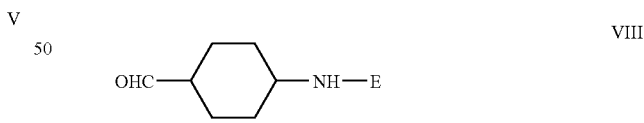

wherein E is A-D (A and D being as defined in formula I) or a protecting group such as Cbz, Alloc or Boc, and, when E is a protecting group, removing the protecting group and reacting the deprotected intermediate with a compound of formula III

L⁰-A-D                                III wherein A and D are as in formula I and L⁰ is appropriate to allow connection of the two moieties NH₂ and A-D of said intermediate and the compound of formula III.

The compounds or formula I thus obtained may, if desired, be converted into their salts, and notably into their pharmaceutically acceptable salts.

Besides, whenever the compounds of formula I are obtained in the form of mixtures of enantiomers, the enantiomers can be separated using methods known to one skilled in the art (e.g. by formation and separation of diastereomeric salts or by chromatography on a chiral stationary phase). Whenever the compounds of formula I are obtained in the form of mixtures of diasteromers they may be separated by an appropriate combination of silica gel chromatography, HPLC and crystallization techniques.

In process alternative a), preferred reactive groups $L^0$ and resulting connections NH-A, as the case may be, are evident from the following Table 1 (wherein Y represents a halogen atom or the group $OSO_2R$ in which R is $CH_3$, $CF_3$ or tolyl):

TABLE 1

| A—$L^0$ | NH—A |
|---|---|
| C(O)—OH | NH—CO |
| C(O)—Cl | NH—CO |
| C(O)—H | NH—$CH_2$ |
| $CH_2$—Y | NH—$CH_2$ |

The compounds of formula I can be prepared by different routes as illustrated in Schemes 1-6 hereafter.

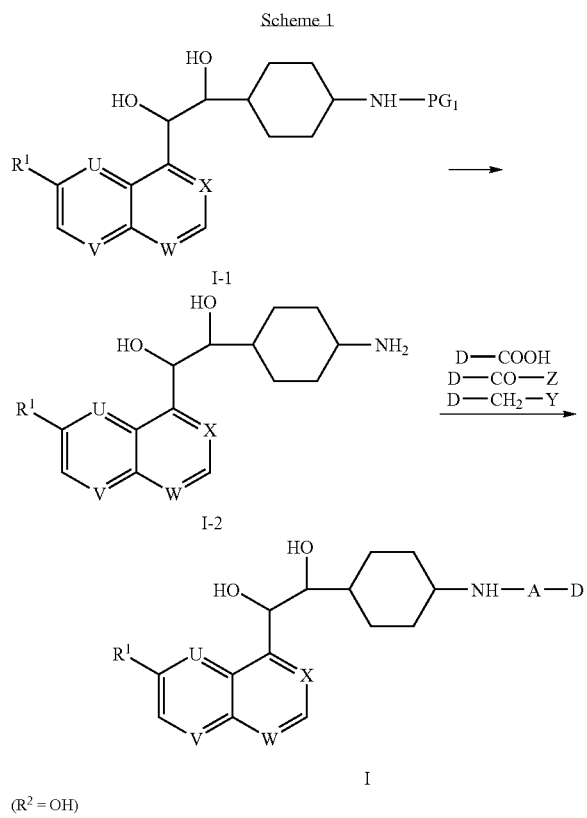

Scheme 1

In Scheme 1, $PG_1$ is a protecting group (e.g. Boc, Alloc or Cbz), Z is H or halogen, Y is halogen or the group $OSO_2R$ in which R is $CH_3$, $CF_3$ or tolyl, and the other symbols have the same meanings as in formula I.

Compounds of formula I wherein A is CO can be obtained from intermediate I-2 (Scheme 1) through reaction with a carboxylic acid derivative (D-COOH), in the presence of an activating agent such as DCC, EDC, HOBT or HATU (G. Benz in *Comprehensive Organic Synthesis*, B. M. Trost, I. Fleming, Eds; Pergamon Press: New York (1991), vol. 6, p. 381) between −20° C. and 60° C. in a dry aprotic solvent like DCM acetonitrile or DMF. Alternatively, the carboxylic acid can be activated by conversion into its corresponding acid chloride by reaction with oxalyl chloride or thionyl chloride neat or in a solvent like DCM between −20° and 60° C.

Compounds of formula I wherein A is $CH_2$ can be obtained from intermediate I-2 after reaction with an aldehyde (D-CHO) and a suitable reducing agent to provide compounds of formula I. The intermediate imine may be formed in a variety of protic or aprotic solvents such as DMF, N,N-dimethylacetamide, 1,2-DCE, MeOH, MeCN, in presence or not of a drying agent such as molecular sieves. The imine is reduced subsequently or simultaneously with a suitable reagent such a $NaBH_4$, sodium triacetoxyborohydride or sodium cyanoborohydride (R. O. and M. K. Hutchins, *Comprehensive Organic Synthesis*, B. M. Trost, I. Fleming, Eds; Pergamon Press: New York (1991), vol. 8, p. 25-78).

Removal of the protecting group ($PG_1$) such as Boc or Cbz on a nitrogen atom in I-1 is carried out under standard acidic conditions to give the corresponding free amine. Alternatively, the Cbz group can be removed under catalytic hydrogenation over Pd/C. Removal of the Alloc protecting group is achieved in presence of a palladium salt such as palladium acetate or $Pd(PPh_3)_4$ and an allyl scavenger such as pyrrolidine, tributylstannane or dimedone in a solvent such as THF, acetone or $CH_3CN$ between 0° and 70° C. The use of protecting groups to mask reactive functionality is wellknown to those of skill in the art, and other protecting groups are listed in reference books such as P. J. Kocienski, 'Protecting Groups', Thieme (1994).

Compounds of formula I wherein A is $CH_2$ can be obtained from intermediate I-2 after reaction with a halogenide, mesylate or tosylate derivative D-$CH_2$Y between −20° C. and 100° C. in a dry aprotic solvent like DCM, MeCN, DMF or THF in presence of a base such as $K_2CO_3$ or DIPEA.

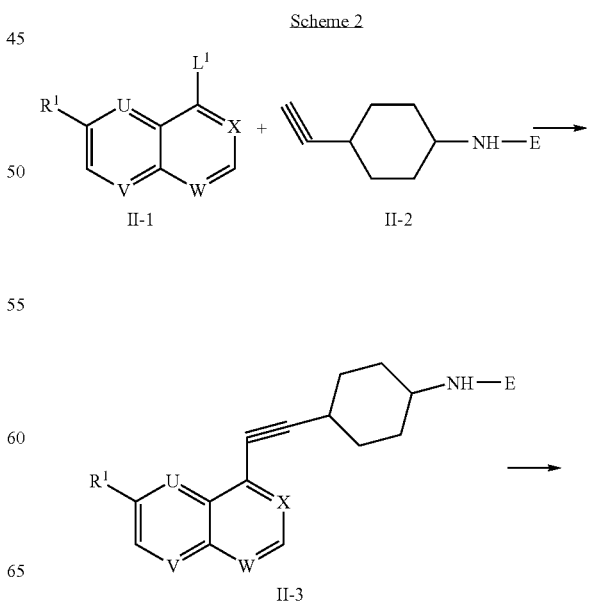

Scheme 2

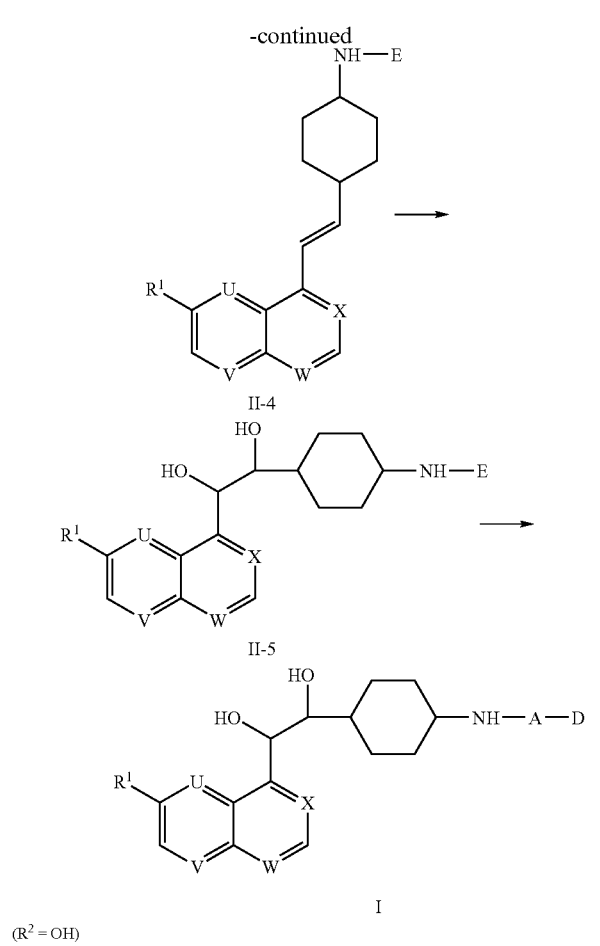

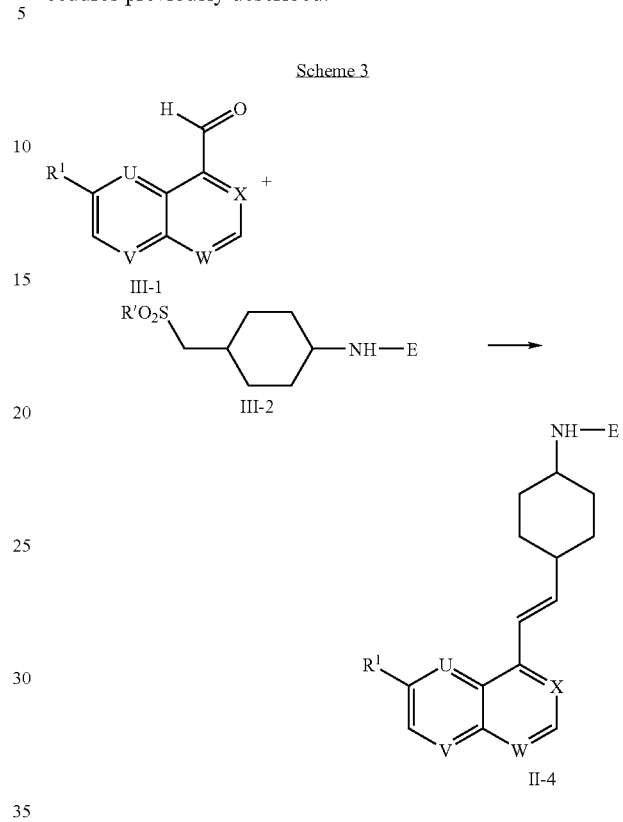

In Scheme 2, $L^1$ is $OSO_2CF_3$ or a halogen atom (preferably Br or Cl), E is a protecting group such as Cbz or Boc, and the other symbols have the same meanings as in formula I. According to the nature of A-D, compounds II-2 wherein E represents A-D can be used in the reaction sequence.

Compounds of formula I can also be obtained from compounds II-5 (Scheme 2) Intermediate II-3 may be obtained from derivative II-1 and a terminal alkyne derivative II-2. The alkyne II-2 and the 4-trifluoromethanesulfonate II-1 are coupled under Sonogashira conditions using catalytic amount of a palladium salt, an organic base such as TEA and a catalytic amount of a copper derivative (usually copper iodide) in a solvent such a DMF between 20° C. to 100° C. (see Sonogashira, K. in *Metal-Catalyzed Reactions*, Diedrich, F., Stang, P. J., Eds; Wiley-VCH: New York (1998)); alternatively, for example when U=V=CH and W=X=N, the 4-trifluoromethanesulfonate II-1 can be replaced by a halogeno derivative II-1 (e.g. $L^1$=Cl). The resulting alkyne II-3 is hydrogenated to the alkene II-4 using methods reviewed by Siegel, S. et al. in *Comprehensive Organic Synthesis*, B. M. Trost, I. Fleming, Eds; Pergamon Press: New York (1991), vol. 8, p. 417-470.

The (E)-alkene II-4 is transformed into the corresponding chiral cis-diol derivative II-5 by treatment with AD mixtures in presence of methanesulfonamide in a water/2-methyl-2-propanol mixture as described in *Chem. Rev.* (1994), 94, 2483. The sense of induction relies on the chiral ligand contained in the mixture, either a dihydroquinine-based ligand in AD-mix α or a dihydroquinidine-based ligand in AD-mix β.

In case E is a protecting group, the protecting group of compound II-5 is removed as before and the resulting free amine is further transformed into the chiral compounds I using procedures previously described.

In Scheme 3, R' may be 1-phenyl-1H-tetrazol-5-yl or benzothiazol-2-yl, E is a protecting group such as Cbz, or Boc and the other symbols have the same meanings as in formula I. According to the nature of A-D, compounds III-2 wherein E represents A-D can be used in the reaction.

Compounds of formula II-4 can also be obtained as an (E)-isomer from an aldehyde derivative III-1 and a sulfone III-2 (Scheme 3) after reaction in presence of KHMDS or LiHMDS in a solvent such as 1,2-DME, DMF or toluene between −78° C. and 0° C. as reviewed by Blakemore, P. R in *J. Chem. Soc., Perkin Trans.* 1 (2002), 2563-2585. The (E)-alkene II-4 is further transformed into the corresponding chiral cis-diol derivative II-5 using procedures previously described.

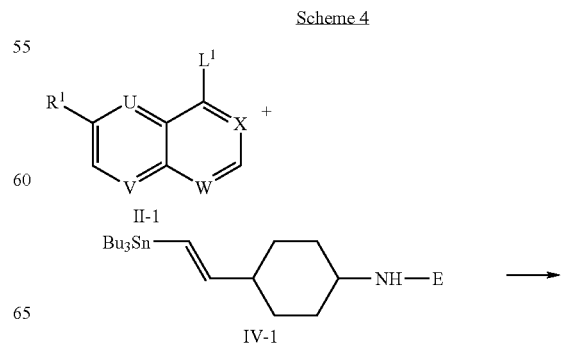

-continued

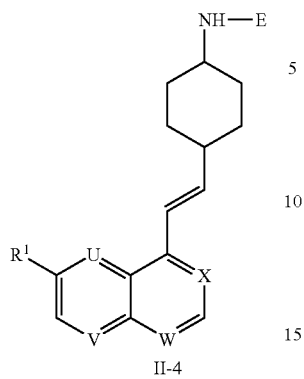

II-4

In Scheme 4, $L^1$ is $OSO_2CF_3$ or halogen, E is a protecting group such as Cbz, or Boc and the other symbols have their above meanings. According to the nature of A-D, compounds IV-1 wherein E represents A-D can be used in the reaction.

An alternate route to obtain (E)-alkene II-4 may be to couple a 4-trifluoromethanesulfonate derivative II-1 ($L^1$=$OSO_2CF_3$; Scheme 4) with an organostannane IV-1 deriving from a terminal alkyne derivative II-2 (Scheme 2). Indeed, the hydrostannation reaction of an alkyne derivative II-2 using tributyl tin hydride and a catalytic amount of either a palladium salt or a molybdenum complex generates an E:Z mixture of the vinylstannane intermediate as described in *J. Org. Chem.* (1990), 55, 1857. The vinylstannane is reacted with a 4-trifluoromethanesulfonate derivative II-1 under Stille coupling conditions (as described in *J. Am. Chem. Soc.* (1987), 109, 5478). Typical reaction conditions involve a palladium salt such as $Pd(PPh_3)_4$ or dichloro bis(triphenylphosphine)palladium, LiCl and a radical scavenger such as 2,6-dimethyl-4-methylphenol in a solvent such as DMF or dioxane at a temperature ranging between 0° C. and 100° C., more preferably at a temperature ranging between 20° C. and 80° C. As the reaction proceeds normally at a faster rate using (E)-vinylstannane, the resulting (E)-alkene II-4 is usually obtained with a high isomeric purity.

Scheme 5

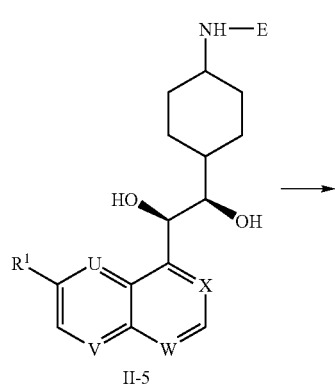

II-5

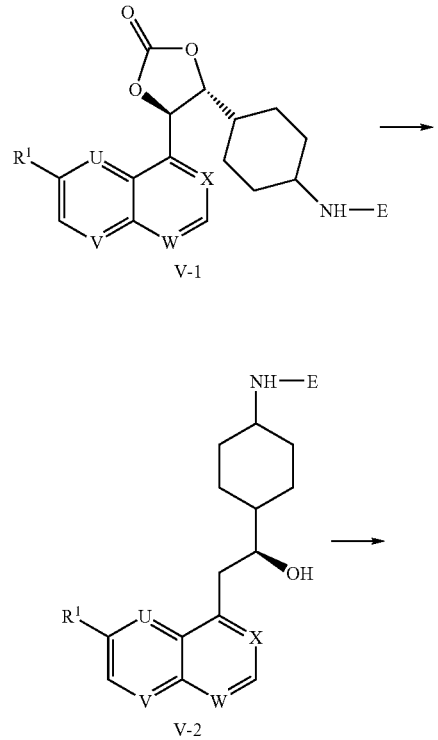

V-1

V-2

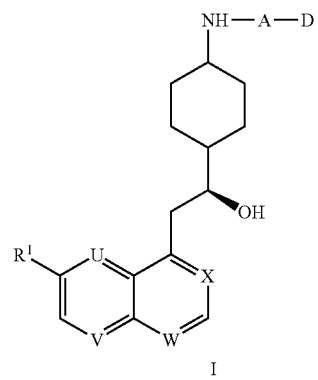

I

In Scheme 5, E is a protecting group such as Cbz or Boc and the other symbols have their above meanings. According to the nature of A-D, compounds II-5 wherein E represents A-D can be used in the reaction sequence.

As illustrated in Scheme 5, the previously mentioned chiral cis-diol II-5 may be transformed into the corresponding cyclic carbonate V-1, by treatment with either phosgene, diphosgene or triphosgene in presence of an organic base such as TEA or pyridine or carbonyldimidazole in an inert solvent such as DCM or THF at a temperature ranging between −78° C. and 50° C., and preferably at a temperature ranging between 0° C. and 20° C. The cyclic carbonate V-1 is subsequently transformed to the homobenzylic alcohol V-2 by hydrogenolysis using catalytic system such as Pd/C in presence of hydrogen in a solvent such as EA. The intermediate V-2 is further transformed into a compound or formula I using procedures previously described.

Scheme 6

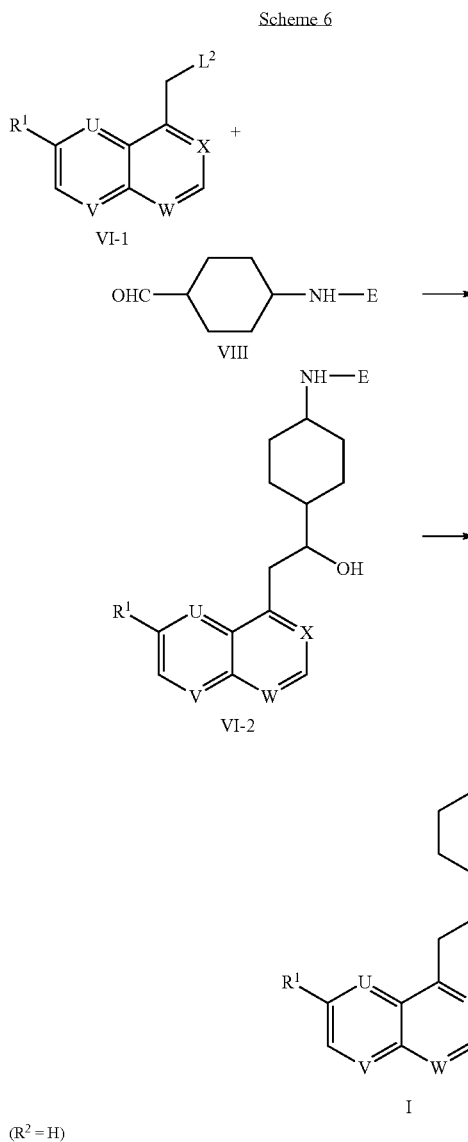

In Scheme 6, $L^2$ is MgCl, MgBr, $L^1$ or K, E is a protecting group such as Alloc, Cbz or Boc, and the other symbols have their above meanings. According to the nature of A-D, compounds VIII wherein E represents A-D can be used in the reaction sequence.

As illustrated in Scheme 6, compounds of formula I wherein $R^2$ is H can be obtained by reacting the aldehyde derivative VIII either with a Grignard reagent VI-1 ($L^2$=MgCl, MgBr) in a dry solvent such as ether or THF between 0° C. and 60° C. or with a lithium or potassium derivative VI-1 ($L^2$=$L^1$, Na or K) in a solvent such as THF or ether between −78° C. and 20° C. The intermediate VI-2 is further transformed into a compound of formula I ($R^2$=H) using procedures already described.

Starting Materials:

The required quinoline, [1,5]-naphthyridine, quinazoline and quinoxaline derivatives II-1, III-1 and VI-1 are prepared following literature procedures. For example, 4-hydroxy-[1,5]-naphthyridines (II-1; $L^1$=OH, U=W=N and V=X=CH) and 4-hydroxy quinolines (II-1; $L^1$=OH, W=N and U=V=X=CH) can be prepared from the corresponding aminopyridines or anilines by reaction with diethyl ethoxymethylene malonate to produce the 4-hydroxycarboxylic acid ester derivative with subsequent hydrolysis to acid, followed by thermal decomposition in inert solvents (J. T. Adams, *J. Am. Chem. Soc.* (1946), 68, 1317). Others routes to such derivatives uses the condensation of substituted aminopyridines or anilines with 2,2-dimethyl-[1,3]dioxane-dione and triethylorthoformate followed by heating of the resulting 2,2-dimethyl-5-[(arylamino)methylidene]-1,3-dioxane-4,6-dione intermediate in refluxing diphenyl ether. Quinazolines ($L^1$=OH, $C_1$, $NH_2$, W=X=N and U=V=CH) may be prepared by standard routes as described by T. A. Williamson in *Heterocyclic Compounds* (1957), 6, 324. 3-substituted quinoxalin-5-ols (II-1; $L^1$=OH, U=V=N and X=W=CH) can be prepared as described by Y. Abe et al. in *J. Med. Chem.* (1998), 41, 4062.

Aldehydes III-1 are prepared following literature procedures or from the corresponding derivatives II-1 ($L^1$=Br) are after treatment with an alkyllithium such as n-BuLi in a solvent like THF at a temperature ranging between −80° C. and −30° C. and subsequent quenching of the lithio species with DMF as described in *J. Org. Chem.* (1980), 45, 1514 (Scheme 7).

Scheme 7

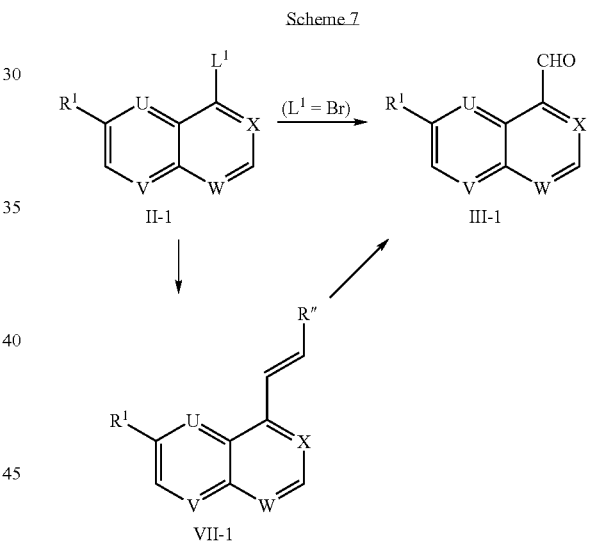

In Scheme 7, $L^1$ represents OTf, Br or Cl, R" is hydrogen, alkyl, aryl, alkoxycarbonyl or arylalkoxycarbonyl, and the other symbols have the same meanings as in formula I.

An alternate route to generate aldehydes III-1 consists in reacting derivative II-1 ($L^1$=OTf, Br or Cl) with trans-phenylvinyl boronic acid under typical Miyaura-Suzuki coupling conditions (see *Synth. Commun.* (1981), 11, 513) employing a palladium salt, an inorganic base such as $K_2CO_3$ or $Na_2CO_3$, in an aq. solvent such as a dioxane-water mixture at a temperature ranging between 20° and 100° C. The alkene derivatives VII-1 can also be obtained from the corresponding bromo derivatives II-1 ($L^1$=Br) by reaction with an alkyl acrylate under Heck conditions in presence of palladium acetate and an organic base as described by S. Chandrasekhar et al. in *Org. Lett.* (2002), 4, 4399-4401. The corresponding alkenes VII-1 may be directly transformed into the aldehydes III-1 by ozonolysis ($O_3$ stream then quenching with either dimethylsulfide or $PPh_3$) or via a cleavage of the intermediate diols using NaIO$_4$ in aq. acetone. The diols are obtained using a catalytic amount of osmium tetroxide in the presence a co-oxidant such as NMO in aq. solvent such as acetone-water or DCM-water (see Cha, J. K. Chem. Rev. (1995), 95, 1761-1795).

Alternatively, the aldehydes III-1 may be obtained by reaction of the bromide II-1 (L$^1$=Br) under CO pressure in presence of a palladium catalyst. The bromide may also be transformed to the aromatic nitrile using conditions reported in J. Org. Chem. (2005), 70, 1508-1510 and subsequent controlled reduction of the nitrile using DIBAH in a solvent such as THF or DCM at a temperature ranging between −78° C. and 20° C., most preferably at a temperature in the vicinity of 0° C.

The required derivatives VI-1 were obtained from the corresponding methyl analogues (L$^2$=H) as follows. Treatment of compounds VI-1 (L$^2$=H) with a strong base such as lithium diisopropylamide or KHMDS in a solvent such as THF or ether between −78° C. and 20° C. afforded the corresponding lithium species (L$^2$=Li or K). Alternatively, treatment of compounds VI-1 (L$^2$=H) with NBS in a solvent such as CCl$_4$ in presence of either a radical initiator such as dibenzoylperoxide or AIBN or of light between 20° C. and 90° C. afforded the corresponding bromo species (L$^2$=Br).

The starting methyl derivatives VI-1 (L$^2$=H) were either commercially available (e.g. 6-methoxy-4-methyl-quinoline) or obtained by treating the corresponding chloro or bromo derivatives II-1 with a strong base such as n-BuLi in a solvent such as THF between −78° C. and −30° C. and subsequent quenching with methyl iodide or dimethylsulfate. The required bromo or chloro derivatives are described in WO 2004/089947 (8-bromo-2-methoxy-quinoline or 5-bromo-3-methoxyquinoline), WO 00/21948 (2-methoxy-8-methyl-1, 5-naphthyridine) or J. Am. Chem. Soc. (1946), 68, 1301-1303 (4-chloro-6-methoxy-quinazoline).

3-methoxy-5-methylquinoxaline is prepared from the corresponding 3-chloro-5-methylquinoxaline (U.S. Pat. No. 3,979,387) after reaction with sodium methoxide in a solvent such as MeOH or DMF between 20° C. and 60° C.

Scheme 8

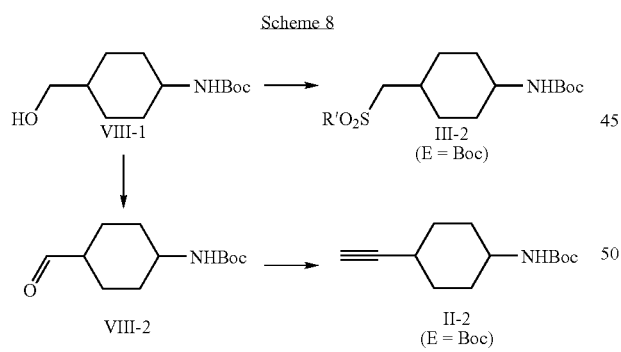

In Scheme 8, R' represents 1-phenyl-1H-tetrazol-5-yl or benzothiazol-2-yl.

The alkyne derivatives II-2 are generally obtained from a suitable alcohol VIII-1 (Scheme 8) which is converted first into the aldehyde VIII-2 using for example the Moffat-Swern (see Synthesis (1981), 165), or the Dess-Martin periodinane (see J. Am. Chem. Soc. (1991), 113, 7277) oxidation protocols. The aldehyde is converted into the corresponding alkyne using either the Corey-Fuchs protocol (formation of the gem-dibromide then treatment with n-BuLi) as described in Tetrahedron Lett. (1972), 3769 or using dimethyl-2-oxopropylphosphonate diazo derivative (so called Ohira's reagent, Synth. Commun. (1989), 19, 561) or dimethyldiazomethylphosphonate as described in Synlett (2003), 59 and Synlett (1996), 521.

The sulfone derivatives III-2 were obtained from the corresponding alcohol derivatives VIII-1 (Scheme 8) via a Mitsunobu coupling (as reviewed in O. Mitsunobu, Synthesis (1981), 1) with 1-phenyl-1H-tetrazole-5-thiol or benzothiazol-2-thiol in the presence of DEAD or DIAD and PPh$_3$. The reaction may be performed in a wide range of solvents such as DMF, THF or DCM and within a wide range of temperatures (between −78° C. and 50° C.). An alternate route to form the intermediate sulphide requires the activation of the alcohol III-2 as for example a tosylate, a triflate or a mesylate by treatment with TsCl, trifluoromethanesulphonic anhydride or MsCl respectively in the presence of an organic base such as TEA between −40° C. and 60° C. in a dry aprotic solvent like DCM, MeCN or THF. Once activated, alcohol III-2 reacts with NaI or KI in acetone at a temperature ranging between 0° C. and 65° C., to form the corresponding iodide. The latter serves as an alkylating agent of the 1-phenyl-1H-tetrazole-5-thiol. The alkylation reaction is performed in presence of an inorganic base such as KOH or NaOH in a solvent such as EtOH at a temperature ranging between −20° C. and 70° C. The resulting intermediate thio derivatives were further oxidized into the corresponding sulfones III-2. A wide range of oxidizing agents may be used to perform such a reaction, such as MCPBA in a solvent such as DCM, Oxone® in a solvent such as aq. MeOH (see Tetrahedron Lett. (1981), 22, 1287), or aq. hydrogen peroxide in presence of ammonium heptamolybdate tetrahydrate in EtOH (see J. Org. Chem. (1963), 28, 1140).

The cyclohexane derivative VIII-1 (R$^2$=H) is commercially available.

Particular embodiments of the invention are described in the following Examples, which serve to illustrate the invention in more detail without limiting its scope in any way.

EXAMPLES

All temperatures are stated in ° C. All analytical and preparative HPLC investigations on non-chiral phases are performed using RP-C18 based columns.

Preparation A 3-methoxy-quinoline-5-carbaldehyde

A.i. 3,5-dibromoquinoline

To concentrated H$_2$SO$_4$ (130 ml) was added dropwise at 0° C., over 80 min, 3-bromoquinoline (50 g) at a rate allowing the internal temperature to be maintained between 0° and 10° C. After the addition was complete, NBS (48 g) was added portionwise and the reaction mixture was stirred at rt overnight. The reaction mixture was poured onto ice (2 l) and the resulting solid was dissolved in DCM (600 ml). The aq. layer was further extracted with DCM (600 ml) and the combined extracts were washed with 1M NaOH (300 ml) and concentrated in vacuo. The residue was adsorbed on SiO$_2$ and the resulting dispersal was loaded on the top of a column and eluted with a DCM-Hex (1-1, 3 l) then DCM (3 l) and finally DCM-ether (1-1, 2 l). The title compound was recovered from the last fraction after evaporation to yield 40 g of a white solid.

$^1$H NMR (CDCl$_3$) δ: 8.94 (d, J=2.2 Hz, 1H); 8.73 (d, J=2.2 Hz, 1H); 8.08 (d, J=8.5 Hz, 1H); 7.88 (d, J=7.5 Hz, 1H); 7.62 (dd, J=7.5, 8.5 Hz, 1H).

A.ii. 5-bromo-3-methoxyquinoline

To a mixture of sodium methoxide (14.5 g) in DMPU (350 ml) heated at 125° C., was added in one portion intermediate A.1 (34.5 g). The reaction was then heated at the same temperature for 1 h. The reaction mixture was then cooled to rt and poured onto ice (300 g). After the ice melted, the solid was filtered off and dried under vacuum. The filtrate was extracted with ether (4×150 ml). The combined extracts were washed with brine and dried over $Na_2SO_4$. After filtration, the solvent was evaporated and the residue purified over $SiO_2$ (Hex-EA 4-1) to afford a material that was pooled with the solid. The material was dissolved in DCM and dried over $Na_2SO_4$. After filtration and evaporation, the solid was further dried under HV to afford the title compound (24.5 g) as a beige solid.

$^1$H NMR ($CDCl_3$) δ: 8.68 (d, J=2.8 Hz, 1H); 8.03 (d, J=8.3 Hz, 1H); 7.80 (d, J=7.5 Hz, 1H); 7.72 (d, J=2.8 Hz, 1H); 7.42 (dd, J=7.5, 8.3 Hz, 1H); 4.02 (s, 3H).

MS (ESI, m/z): 239.7 $[M+H]^+$.

A.iii. 3-methoxy-quinoline-5-carbaldehyde

To a solution of intermediate A.ii (10 g) in THF (250 ml) cooled to −78° C., was added n-BuLi (22 ml). After 15 min, a solution of DMF (10 ml) in ether (20 ml) was quickly added. The solution was stirred 15 min and EtOH (5 ml), followed by 1M $NaHSO_4$ (40 ml), was added. After warming to rt, the organic layer was diluted with EA (100 ml). The two layers were separated and the aq. layer was extracted once with EA (100 ml). The combined org. layers were washed with brine and concentrated to dryness. The residue was chromatographed (EA-Hex 1-2 then 1-1) to afford the title compound (4.75 g) as a yellowish solid.

$^1$H NMR ($CDCl_3$) δ: 10.32 (s, 1H); 9.02 (d, J=2.9 Hz, 1H); 8.75 (d, J=2.9 Hz, 1H); 8.31 (d, J=8.3 Hz, 1H); 8.02 (d, J=7.1 Hz, 1H); 7.72 (dd, J=7.1, 8.3 Hz, 1H); 4.02 (s, 3H).

MS (ESI, m/z): 187.9 $[M+H]^+$.

Preparation B

3-methoxy-quinoxaline-5-carbaldehyde

B.i. 2-cyano-N-(2-methyl-6-nitro-phenyl)-acetamide

To a solution of 2-methyl-6-nitroaniline (25 g, 164.3 mmol) in benzene (200 ml) were added cyanoacetic acid (14.5 g, 170.46 mmol) and $PCl_5$ (35 g, 168 mmol). The reaction mixture was heated at 60° C. for 7 h. After cooling to rt, the reaction mixture was filtered and the solid was washed with benzene and water. The solid was dried under reduced pressure to afford the title acetamide (24 g, 109 mmol) as a yellow solid.

$^1$H NMR (d6-DMSO) δ: 10.2 (s, 1H); 7.78 (d, J=8.3 Hz, 1H); 7.65 (d, J=8.3 Hz, 1H); 7.43 (t, J=8.3 Hz, 1H); 3.95 (s, 2H); 2.30 (s, 3H).

B.ii. 3-hydroxy-5-methyl-1-oxy-quinoxaline-2-carbonitrile

To a solution mixture of intermediate B.i (24 g, 109.5 mmol) in 1M aq. NaOH (100 ml) was added pyridine (100 ml). The reaction mixture was stirred at rt for 4 h. The pH was adjusted to 6 by addition of 1M aq. HCl. The solid was filtered off and washed with water. The solid was triturated with EtOH. After drying under HV, the title nitrile (17.7 g, 87.9 mmol) was obtained as a yellow solid.

MS (ESI, m/z): 202.1 $[M+H]^+$.

B.iii. 8-methyl-quinoxalin-2-ol

To a solution of intermediate B.ii (17.7 g, 87.9 mmol) in water (300 ml) and EtOH (24 ml) was added sodium dithionite (35.4 g, 203.9 mmol). The reaction mixture was heated at 60° C. for 1 h. The reaction mixture was filtered till warm, and the pH of the filtrate was adjusted to 2 by adding 1M aq. HCl. The pH of the solution was subsequently made basic by adding solid NaOH (10 g). EA (150 ml) was added. The aq. layer was extracted twice more with EA (2×150 ml). The combined organic extracts were dried over $Na_2SO_4$, filtered and concentrated to dryness. The residue was dried under HV to afford the title intermediate (11.1 g, 69 mmol) as a yellow solid.

$^1$H NMR (d6-DMSO) δ: 11.75 (br s, 1H); 8.17 (s, 1H); 7.62 (d, J=8.4 Hz, 1H); 7.40 (d, J=8.4 Hz, 1H); 7.21 (t, J=8.4 Hz, 1H); 2.42 (s, 3H).

MS (ESI, m/z): 161.1 $[M+H]^+$.

B.iv. 2-chloro-8-methyl-quinoxaline

A solution of intermediate B.iii (11.1 g, 69.5 mmol) in phosphorus oxychloride (80 ml) was heated at 110° C. during 2 h. After cooling to rt, the reaction mixture was poured onto ice (200 g). The aqueous layer was extracted with EA (2×200 ml). The combined extracts were washed with brine (100 ml), dried over $Na_2SO_4$, filtered and concentrated to dryness. The residue was chromatographed over $SiO_2$ (Hex-EA 1-1) to afford the title intermediate (12.5 g, 69.5 mmol) as a red solid.

$^1$H NMR (d6-DMSO) δ: 8.99 (s, 1H); 7.97 (m, 1H); 7.80 (m, 2H); 2.68 (s, 3H).

MS (ESI, m/z): 179.2 $[M+H]^+$.

B.v. 2-methoxy-8-methyl-quinoxaline

To a solution of intermediate B.iv (12.5 g, 69.5 mmol) in DMF (80 ml) was added sodium methoxide (9 g, 166 mmol). The reaction mixture was heated at 45° C. for 4 h. After cooling to rt, the reaction mixture was partitioned between water (10 ml) and EA (200 ml). The organic layer was washed once with water (100 ml), dried over $Na_2SO_4$, filtered and concentrated to dryness. The residue was chromatographed over $SiO_2$ (Hex-EA 1-4) to afford the title intermediate (10.2 g, 58.55 mmol) as a yellow solid.

$^1$H NMR ($CDCl_3$) δ: 8.48 (s, 1H); 7.88 (d, J=7.9 Hz, 1H); 7.55 (d, J=7.9 Hz, 1H); 7.47 (t, J=7.9 Hz, 1H); 4.12 (s, 3H); 2.69 (s, 3H).

MS (ESI, m/z): 175.4 $[M+H]^+$.

B.vi. 8-dibromomethyl-2-methoxy-quinoxaline

To a solution of intermediate B.v (10.2 g) in $CCl_4$ (560 ml) were added AIBN (0.96 g) and NBS (25.9 g, 145.5 mmol). The reaction mixture was heated at 80° C. for 3 h. After cooling to rt, the reaction mixture was washed with water (200 ml) and the organic layer was dried over $Na_2SO_4$, filtered and concentrated in vacuo. The residue was triturated with MeOH to give, after drying under HV, the title dibromide (14.4 g, 43.3 mmol) as a slightly beige solid.

$^1$H NMR (d6-DMSO) δ: 8.69 (s, 1H); 8.25 (dd, J=1.3, 7.5 Hz, 1H); 8.07 (dd, J=1.3, 8.3 Hz, 1H); 8.02 (s, 1H); 7.74 (dd, J=7.5, 8.3 Hz, 1H); 4.14 (s, 3H).

MS (ESI, m/z): 332.8 $[M+H]^+$.

B.vii. 3-methoxy-quinoxaline-5-carbaldehyde

To a solution of intermediate B.vi (10.7 g, 32.2 mmol) in EtOH (330 ml) was added, at rt, a solution of silver nitrate (15 g) in water (70 ml). The reaction was stirred at rt for 1 h. The reaction mixture was diluted with MeCN (200 ml) and the solids were filtered off and the filtrate was concentrated in vacuo. The residue was filtered over a $SiO_2$ pad (eluent: EA) to afford the title aldehyde (6.2 g, 32.2 mmol) as a slightly yellow solid.

$^1$H NMR (d6-DMSO) δ: 11.15 (s, 1H); 8.74 (s, 1H); 8.36 (dd, J=1.3, 8.1 Hz, 1H); 8.21 (dd, J=1.3, 7.9 Hz, 1H); 7.80 (dd, J=7.9, 8.1 Hz, 1H); 4.14 (s, 3H).

MS (ESI, m/z): 189.2 [M+H]$^+$.

Preparation C

(E)-3-(2,5-difluoro-phenyl)-propenal

C.i. (E)-3-(2,5-difluoro-phenyl)-acrylic acid ethyl ester

To an iced chilled suspension of NaH (1.13 g, 60% in oil dispersion, 28.2 mmol) in THF (32 ml) was added triethylphosphonoacetate (5.6 ml, 28.2 mmol). The reaction mixture was stirred at rt for 20 min. 2,5-difluoro-benzaldehyde (3.34 g, 23.5 mmol) was added drop wise. After 30 min, 10% aq. $NaHSO_4$ (100 ml) was added and the mixture was diluted with EA (150 ml). The two phases were separated and the aq. layer was extracted twice with EA (2×100 ml). The combined org. layers were washed with brine (100 ml), dried over $Na_2SO_4$, filtered and concentrated to dryness. The residue was chromatographed over $SiO_2$ (Hex-EA 19-1) to afford the title unsaturated ester (5.0 g, 100%) as colourless oil.

$^1$H NMR (CDCl$_3$): 7.76 (dd, J=1, 16.1 Hz, 1H); 7.26-7.21 (m, 1H); 7.13-7.03 (m, 2H); 6.52 (d, J=16.1 Hz, 1H); 4.29 (q, J=7.1 Hz, 2H); 1.36 (t, J=7.1 Hz, 3H).

C.ii. (E)-3-(2,5-difluoro-phenyl)-prop-2-en-1-ol

To a solution of intermediate C.i (5.0 g, 23.5 mmol) in ether (100 ml), cooled to 0° C., was added a solution of DIBAH (1M in Hex, 60 ml, 60 mmol). The mixture was stirred at the same temperature for 40 min. Water (6 ml) was added and the mixture was stirred 30 min. The solid was filtered off and thoroughly washed with ether. The filtrate was concentrated to dryness to afford the title alcohol (4.0 g, 98% yield) as colourless oil.

$^1$H NMR (CDCl$_3$): 7.15 (ddd, J=3.1, 5.9, 9.0 Hz, 1H); 7.00 (td, J=4.6, 9.0 Hz, 1H); 6.95-6.87 (m, 1H); 6.75 (dd, J=1.3, 16.1 Hz, 1H); 6.45 (td, J=5.3, 16.1 Hz, 1H); 4.38 (br d, J=5.3 Hz, 2H); 1.63 (s, 1H).

C.iii. (E)-3-(2,5-difluoro-phenyl)-propenal

To a solution of intermediate C.ii (1.70 g, 10 mmol) in DCM (20 ml) was added at rt, a solution of Dess-Martin periodinane (15 wt % in DCM, 20 ml). The mixture was stirred at rt for 3 h. After concentration to dryness, the residue was chromatographed over $SiO_2$ (Hex-EA 9-1) to afford the title aldehyde (1.06 g, 63% yield) as a white solid.

$^1$H NMR (d6-DMSO): 9.74 (d, J=7.6 Hz, 1H); 7.88-7.81 (m, 1H); 7.79 (overlapped dd, J=1.4, 16.0 Hz, 1H); 7.46-7.37 (m, 2H); 6.67 (dd, J=7.6, 16.0 Hz, 1H).

Preparation D

8-fluoro-6-methoxy-quinoline-4-carbaldehyde

D.i. 4-bromo-8-fluoro-6-methoxy-quinoline

To a solution of 8-fluoro-6-methoxy-quinolin-4-ol (13.2 g, 68.3 mmol; prepared as in WO 2004/041210) in DMF (70 ml), heated to 40° C. in a water-bath, was added $PBr_3$ (7 ml, 75 mmol). The mixture was stirred at this temperature for 1 h. The reaction mixture was diluted with water (0.5 l) and saturated $NaHCO_3$ was added until pH 8 was reached. The solids were filtered off, taken up in EA and evaporated with silica gel (40 g). The material was eluted (Hex-EA 3-1) to afford the title bromide (7.0 g, 40% yield) as a yellow solid.

$^1$H NMR (d6-DMSO) δ: 8.60 (d, J=4.6 Hz, 1H); 8.00 (d, J=4.6 Hz, 1H); 7.48 (dd, J=2.6, 11.9 Hz, 1H); 7.24 (dd, J=1.1, 2.6 Hz, 1H); 3.96 (s, 3H).

D.ii. (E)-3-(8-fluoro-6-methoxy-quinolin-4-yl)-acrylic acid ethyl ester

To a solution of intermediate D.i (2.5 g, 9.76 mmol) were added TEA (5 ml), P(o-tolyl)$_3$ (0.254 g, 9 mol %), palladium acetate (0.045 g, 2 mol %) and then ethyl acrylate (5 ml). The mixture was heated at 100° C. for 4 h. The reaction mixture was cooled to rt, diluted with water (300 ml). The solids were filtered off, washed with water (200 ml). The solid was taken up in DCM (300 ml), washed with brine, dried over $Na_2SO_4$, filtered and concentrated to dryness. The residue was chromatographed (Hept-EA 1-1) to afford the title unsaturated ester (2.4 g, 89% yield) as a yellow solid.

$^1$H NMR (d6-DMSO) d: 8.79 (d, J=4.5 Hz, 1H); 8.34 (d, J=15.8 Hz, 1H); 7.92 (d, J=4.5 Hz, 1H); 7.40 (dd, J=2.5, 12.0 Hz, 1H); 7.33 (m, 1H); 6.90 (d, J=15.8 Hz, 1H); 4.26 (q, J=7.1 Hz, 2H); 3.98 (s, 3H); 1.30 (t, J=7.1 Hz, 3H).

D.iii. (2S,3R)-3-(8-fluoro-6-methoxy-quinolin-4-yl)-2,3-dihydroxy-propionic acid ethyl ester Starting from intermediate D.ii. (2.4 g, 8.71 mmol), the title diol (1.6 g, 5.1 mmol) was obtained as a colorless foam using the procedure described in Example 2, step 2.iv. The compound was purified by chromatography using EA-Hept 4-1 as an eluent.

MS (ESI, m/z): 310.0 [M+H]$^+$.

D.iv. 8-fluoro-6-methoxy-quinoline-4-carbaldehyde

To a solution of intermediate D.iii (1.6 g, 5.17 mmol) in acetone (40 ml) was added a solution of $NaIO_4$ (2.6 g, 12.1 mmol) in water (10 ml). The mixture was stirred at rt for 40 min. Water (100 ml) was added and the volatiles were removed in vacuo. The residue was filtered and washed thoroughly with water. The solid was collected and dried under HV to afford the title aldehyde (0.8 g, 75% yield) as a yellow solid.

¹H NMR (d6-DMSO) δ: 10.51 (s, 1H); 9.09 (d, J=4.2 Hz, 1H); 8.21 (dd, J=1.1, 2.6 Hz, 1H); 8.10 (d, J=4.2 Hz, 1H); 7.47 (dd, J=2.6, 12.0 Hz, 1H); 3.96 (s, 3H).

Preparation E

3-fluoro-6-methoxy-[1,5]naphthyridine-4-carbaldehyde

E.i. trans-7-fluoro-2-methoxy-8-styryl-[1,5]naphthyridine 8-bromo-7-fluoro-2-methoxy-[1,5]naphthyridine (prepared as in WO 2004/058144; 7 g, 27.2 mmol), trans-phenylvinyl boronic acid (4.23 g, 1.05 eq) and $K_2CO_3$ (4.9 g) were introduced in a two-necked flask. The atmosphere was flushed with nitrogen and dioxane (40 ml) and water (10 ml) were added. The mixture was stirred at rt for 5 min and $Pd(PPh_3)_4$ (1.56 g, 5 mol %) was added. The mixture was heated at reflux overnight. After cooling, the solvent was evaporated in vacuo and the residue was extracted with EA (2×150 ml). The combined extracts were washed with brine, dried over $Na_2SO_4$, filtered and concentrated to dryness. The residue was chromatographed (Hept-EA 2-1) to afford the title compound (7.2 g, 94% yield) as a white solid.

MS (ESI, m/z): 281.0 $[M+H]^+$.

E.ii. 1-(3-fluoro-6-methoxy-[1,5]naphthyridin-4-yl)-2-phenyl-ethane-1,2-diol

The title diol (7.6 g, 94% yield) was obtained as a white foam, starting from intermediate E.i (7.2 g, 8.9 mmol) and using the procedure of Example 2, step 2.iv. The compound was purified by chromatography using EA as an eluent.

¹H NMR (CDCl₃) δ: 8.42 (d, J=0.7 Hz, 1H); 8.28 (d, J=9.1 Hz, 1H); 7.24-7.15 (m, 4H); 7.08 (m, 2H); 6.70 (br s, 1H); 5.28 (br s, 1H); 5.10 (d, J=7.9 Hz, 1H); 4.11 (s, 3H); 3.85 (br s, 1H).

E.iii. 3-fluoro-6-methoxy-[1,5]naphthyridine-4-carbaldehyde

To a solution of intermediate E.ii (7.6 g, 23.95 mmol) in acetone (150 ml) was added a solution of $NaIO_4$ (12.8 g) in water (30 ml). The mixture was stirred at rt for 1 h. The solvent was removed in vacuo and the residue was diluted with water (500 ml). The resulting solid was filtered off, thoroughly washed with water, collected and dried under HV to afford the title aldehyde (4.0 g) as a light beige solid.

¹H NMR (d6-DMSO) δ: 11.08 (s, 1H); 9.01 (d, J=1.3 Hz, 1H); 8.41 (d, J=9.1 Hz, 1H); 7.37 (d, J=9.1 Hz, 1H); 4.09 (s, 3H).

MS (ESI, m/z): 206.9 $[M+H]^+$.

Example 1

6-({trans-4-[(1RS)-1-hydroxy-2-(3-methoxy-quinolin-5-yl)-ethyl]-cyclohexylamino}-methyl)-4H-pyrido[3,2-b][1,4]thiazin-3-one 1.i. Toluene-4-sulfonic acid trans-4-tert-butoxycarbonylamino-cyclohexylmethyl ester To an ice-chilled solution of trans-(4-hydroxymethyl-cyclohexyl)-carbamic acid tert-butyl ester (7.06 g, 30.8 mmol) in DCM (120 ml) and THF (30 ml) were added TEA (8.5 ml, 2 eq.) and TsCl (7 g, 1.2 eq.). The mixture was then stirred at rt overnight. DMAP (1 g) was added and the reaction proceeded for 2 h. Saturated $NaHCO_3$ (100 ml) was added. The org. layer was further washed with saturated $CuSO_4$ (2×100 ml), water (100 ml) and brine. The org. layer was then concentrated to dryness. The resulting solid was filtered off, washed with water and dried under vacuum. The title tosylate (11.7 g, 99% yield) was obtained as a white solid.

MS (ESI, m/z): 384.3 $[M+H]^+$.

1.ii. trans-(4-iodomethyl-cyclohexyl)-carbamic acid tert-butyl ester

To a solution of intermediate 1.i (11.7 g, 30.5 mmol) in acetone (100 ml) was added NaI (13.7 g, 3 eq.). The solution was heated at 60° C. overnight. The reaction mixture was concentrated to dryness and the residue was taken up in water, filtered off and the solid was thoroughly washed with water. The solid was collected and dried under high vacuum to afford the title iodide as a white solid (10.2 g, 98% yield).

MS (ESI, m/z): 340.1 $[M+H]^+$.

1.iii. trans-[4-(1-phenyl-1H-tetrazol-5-ylsufanylmethyl)-cyclohexyl]-carbamic acid tert-butyl ester To a solution of 1-phenyl-1H-tetrazole-5-thiol (5.84 g, 32.8 mmol) in EtOH (65 ml) was added powdered KOH (2 g, 35.7 mmol) and the resulting mixture was stirred 1 h under reflux. Intermediate 1.ii (10.1 g, 29.8 mmol) was then added and the reaction stirred at reflux overnight. The reaction mixture was cooled to rt and concentrated to dryness. The residue was resuspended in water, filtered, washed with water, and dried to a constant weight (11.15 g, 96% yield).

¹H NMR (d6-DMSO) δ: 7.66 (br s, 5H); 6.70 (br d, J=7.9 Hz, 1H); 3.24 (d, J=6.8 Hz, 2H); 3.18 (m, 1H); 1.82-1.75 (m, 4H); 1.58 (m, 1H); 1.36 (s, 9H); 1.36-1.01 (m, 4H).

MS (ESI, m/z): 340.1 $[M+H]^+$.

1.iv. trans-[4-(1-phenyl-1H-tetrazole-5-sulfonylmethyl)-cyclohexyl]-carbamic acid tert-butyl ester To a stirred solution of intermediate 1.iii (11.2 g, 28.6 mmol) in EtOH (265 ml) was added at rt a solution of ammonium molybdate heptahydrate (4.4 g, 3.6 mmol) in 30% aq. hydrogen peroxide (38 ml). The reaction was stirred at rt for 3 h, before heating at 75° C. for 1 h. The solvent was carefully removed under reduced pressure and the solid was diluted with water, filtered and washed with water. The title sulfone was further dried to a constant weight (11 g, 91% yield).

¹H NMR (CDCl₃) δ: 7.63-7.49 (m, 5H); 4.82 (br s, 1H); 4.30 (m, 1H); 3.60 (d, J=6.0 Hz, 2H); 3.35 (m, 1H); 2.06-1.96 (m, 4H); 1.36 (s, 9H); 1.28-1.04 (m, 4H).

1.v. trans-{4-[(E)-2-(3-methoxy-quinolin-5-yl)-vinyl]-cyclohexyl}-carbamic acid tert-butyl ester To a solution of intermediate 1.iv (7.92 g, 18.8 mmol) in DMF (75 ml) and HMPT (25 ml) cooled to −35° C., was added drop wise LiHMDS (1M in THF, 30 ml). After the addition was complete, a solution of 3-methoxy-quinoline-5-carbaldehyde (see Preparation A, 3.2 g) in DMF (75 ml) and HMPT (25 ml) was added dropwise. The reaction was allowed to warm up gradually over 2 h 30. Water (200 ml) was added. The mixture was then extracted with ether (4×200 ml). The combined org. layers were concentrated to dryness and the residue was chromatographed (Hex-EA 2-1 then DCM- MeOH 19-1) to afford a white solid that was further triturated with Hex to give the title alkene (1.8 g, 27% yield).

¹H NMR (CDCl₃) δ: 8.70 (d, J=2.8 Hz, 1H); 7.96 (d, J=8.1 Hz, 1H); 7.62-7.49 (m, 3H); 6.94 (d, J=15.4 Hz, 1H); 6.19 (dd, J=7.1, 15.4 Hz, 1H); 4.42 (m, 1H); 3.99 (s, 3H); 3.49 (m, 1H); 2.22 (m, 1H); 2.19-2.10 (m, 2H); 2.00-1.95 (m, 2H); 1.48 (s, 9H); 1.48-1.34 (m, 2H); 1.30-1.21 (m, 2H).

MS (ESI, m/z): 383.3 [M+H]⁺.

1.vi. trans-{4-[rac-1,2-dihydroxy-2-(3-methoxy-quinolin-5-yl)-ethyl]-cyclohexyl}-carbamic acid tert-butyl ester To a solution of intermediate 1.v (1 g, 2.62 mmol) in DCM (20 ml) and water (2 ml) was added NMO (1.04 g, 7.84 mmol) and potassium osmate dihydrate (0.05 g, 0.13 mmol). The reaction was stirred for 5 h at rt. The precipitate that formed during the reaction was filtered off, washed with DCM and water and dried to a constant weight. The title diol (1.05 g, 99% yield) was obtained as a white solid.

¹H NMR (d6-DMSO) δ: 8.65 (d, J=2.7 Hz, 1H); 7.85 (d, J=7.9 Hz, 1H); 7.79 (d, J=2.7 Hz, 1H); 7.65 (d, J=6.0 Hz, 1H); 7.55 (dd, J=6.0, 7.9 Hz, 1H); 6.61 (d, J=8.4 Hz, 1H); 5.34 (br s, 1H); 5.27 (br s, 1H); 4.45 (br d, J=6.4 Hz, 1H); 3.93 (s, 3H); 3.40 (m, 1H); 3.12 (m, 1H); 1.90 (m, 1H); 1.78-1.75 (m, 3H); 1.36 (s, 9H); 1.36-0.95 (m, 5H).

MS (ESI, m/z): 417.0 [M+H]⁺.

1.vii. trans-{4-[5-(3-methoxy-quinolin-5-yl)-2-oxo-[1,3]dioxolan-4-yl]-cyclohexyl}-carbamic acid tert-butyl ester To a solution of intermediate 1.vi (1.05 g, 2.6 mmol) in DCM (15 ml) was added TEA (0.787 ml, 5.6 mmol). The solution was cooled to 0° C. and triphosgene was added (0.84 g, 2.8 mmol) in one portion. The reaction mixture was stirred 30 min at this temperature then at rt. After 4 h, triphosgene (0.42 g) was added and the reaction mixture stirred for 4 h. The reaction mixture was concentrated to dryness and purified by column chromatography (DCM-3% MeOH containing 0.5% aq. NH₄OH) to afford the title cyclic carbonate (0.92 g, 79% yield).

MS (ESI, m/z): 443.0 [M+H]⁺.

1.viii. trans-{4-[J-hydroxy-2-(3-methoxy-quinolin-5-yl)-ethyl]-cyclohexyl}-carbamic acid tert-butyl ester To a solution of intermediate 1.vii (0.921 g, 2.08 mmol) in EA (80 ml) was added 10% Pd/C (0.65 g) and the suspension was stirred under hydrogen atmosphere for 8 h. The catalyst was filtered off and the filtrate concentrated in vacuo. The residue was purified by column chromatography (DCM-MeOH 19-1) to afford the title compound (0.315 g, 37% yield) as a white foam.

¹H NMR (CDCl₃) δ: 8.68 (d, J=2.8 Hz, 1H); 7.97 (d, J=8.3 Hz, 1H); 7.57 (d, J=2.8 Hz, 1H); 7.52 (dd, J=7.0, 8.3 Hz, 1H); 7.42 (d, J=7.0 Hz, 1H); 4.42 (m, 1H); 3.97 (s, 3H); 3.72 (m, 1H); 3.45 (m, 1H); 3.34 (dd, J=2.8, 14.0 Hz, 1H); 2.98 (dd, J=10.0, 14.0 Hz, 1H); 2.16-1.95 (m, 4H); 1.51-1.13 (m, 6H); 1.47 (s, 9H).

MS (ESI, m/z): 400.9 [M+H]⁺.

1.ix. trans-rac-1-(4-amino-cyclohexyl)-2-(3-methoxy-quinolin-5-yl)-ethanol

A solution of intermediate 1.viii (0.315 g, 0.79 mmol) in TFA (5 ml) was stirred for 5 min. The solution was concentrated to dryness, basified with 1M aq. NaOH, diluted with DCM-MeOH 9-1 and the phases separated. The aq. layer was extracted 6 times with DCM-MeOH 9-1. The combined org. layers were dried over Na₂SO₄, filtered and concentrated to dryness. The residue was purified by column chromatography (DCM-MeOH 9-1 containing 1% aq. NH₄OH to 4-1 containing 1% aq. NH₄OH) to afford the title amine (0.237 g, 99% yield) as a white foam.

MS (ESI, m/z): 301.2 [M+H]⁺.

1.x. 6-({trans-4-[(1RS)-1-hydroxy-2-(3-methoxy-quinolin-5-yl)-ethyl]-cyclohexylamino}-methyl)-4H-pyrido[3,2-b][1,4]thiazin-3-one To a solution of intermediate 1.x (0.236 g, 0.79 mmol) in MeOH (6 ml) and 1,2-DCE (12 ml) were added 3 Å molecular sieves (4.8 g) and 3-oxo-3,4-dihydro-2H-pyrido[3,2-b][1,4]thiazine-6-carbaldehyde (prepared as described in WO 2004/002992, 0.168 g, 0.87 mmol). The mixture was stirred at 50° C. overnight. NaBH₄ (0.24 g, 6.35 mmol) was added and the reaction was stirred 2 h. The reaction mixture was filtered through Hydromatrix® (treated with saturated NaHCO₃) and the filtrate concentrated in vacuo. The residue was purified by column chromatography (DCM-MeOH 19-1 containing 1% aq. NH₄OH then 9-1 containing 1% aq. NH₄OH) to afford the title compound (0.255 g, 67% yield) as a white foam.

¹H NMR (d6-DMSO) δ: 10.86 (s, 1H); 8.64 (d, J=2.7 Hz, 1H); 7.81 (d, J=8.3 Hz, 1H); 7.74-7.71 (m, 2H); 7.49 (dd, J=7.0, 8.1 Hz, 1H); 7.41 (d, J=7.0 Hz, 1H); 7.09 (d, J=8.3 Hz, 1H); 4.47 (d, J=6.0 Hz, 1H); 3.95 (s, 3H); 3.74 (s, 2H); 3.52 (s, 2H); 3.52 (m, 1H); 3.22 (dd, J=2.9, 13.5 Hz, 1H); 2.93 (dd, J=7.8, 13.5 Hz, 1H); 2.33 (m, 1H); 2.20-1.92 (m, 4H); 1.72 (m, 1H); 1.39-0.83 (m, 5H).

MS (ESI, m/z): 479.3 [M+H]⁺.

Example 2

3-oxo-3,4-dihydro-2H-pyrido[3,2-b][1,4]thiazine-6-carboxylic acid trans-{4-[(1R,2R)-1,2-dihydroxy-2-(6-methoxy-[1,5]naphthyridin-4-yl)-ethyl]-cyclohexyl}-amide 2.i. trans-(4-ethynyl-cyclohexyl)-carbamic acid tert-butyl ester To a solution of p-toluenesulfonyl azide (10.57 g, 53.1 mmol) in MeCN (660 ml) were added K₂CO₃ (18.6 g, 134.5 mmol) and (2-oxo-propyl)-phosphonic acid dimethyl ester (7.3 ml, 53.1 mmol). The slurry was stirred at rt for 2 hours and a solution of (4-formyl-cyclohexyl)-carbamic acid tert-butyl ester (8.5 g, 37.4 mmol) in MeOH (100 ml) was added and the reaction proceeded overnight. The solvent was removed in vacuo. The residue was partitioned between water (100 ml) and EA (150 ml). The aq. layer was further extracted twice with EA (2×150 ml). The combined extracts were washed with brine and concentrated to dryness. The residue was chromatographed (Hex-EA 3-1) to afford the title alkyne (4.6 g, 55% yield) as a white solid.

¹H NMR (CDCl₃) δ: 4.45 (br s, 1H); 3.48 (br s, 1H); 2.23 (m, 1H); 2.07-1.99 (m, 5H); 1.6-1.46 (m, 2H); 1.46 (s, 9H); 1.2-1.06 (m, 2H).

2.ii. [(E)-4-(2-tributylstannanyl-vinyl)-cyclohexyl]-carbamic acid tert-butyl ester To a solution of intermediate 2.i (4.6 g, 20.6 mmol) in THF (70 ml) were added Cl₂Pd(PPh₃)₂ (0.29 g, 0.41 mmol) and drop wise n-tributyltin hydride (6.6 ml, 24.9 mmol). The reaction proceeded for 30 min. After evaporation to dryness, the residue was chromatographed (Hex-EA 9-1) to afford the title stannane (7.5 g, 70% yield) as a thick oil.

$^1$H NMR (CDCl$_3$) δ: 5.88 (m, 1H); 4.25 (br s, 1H); 3.35 (br s, 1H); 2.07-0.76 (m, 46H, including 1.47 (s, 9H)).

2.iii. trans-{4-[(E)-2-(6-methoxy-[1,5]naphthyridin-4-yl)-vinyl]-cyclohexyl}-carbamic acid tert-butyl ester To a solution of intermediate 2.ii (4.08 g, 7.92 mmol) and trifluoro-methanesulfonic acid 6-methoxy-[1,5]naphthyridin-4-yl ester (2.29 g, 7.44 mmol; prepared as described in WO 03/064421) in 1,4-dioxane (40 ml) were added successively LiCl (0.93 g, 22.00 mmol), 2,6-di-tert-butyl-4-methylphenol (few seeds) and Pd(PPh$_3$)$_4$ (0.168 g, 0.144 mmol). The reaction mixture was then stirred at 100° C. for 5 h. The reaction mixture was cooled to rt, filtered and the volatiles were removed under reduced pressure. The residue was washed with water. The solids were filtered off, air-dried and triturated with EA-Hex 1-9, to afford the title compound (2.84 g, 7.40 mmol) as a white solid.

$^1$H NMR (d6-DMSO) δ: 8.68 (d, J=4.7 Hz, 1H); 8.23 (d, J=9.0 Hz, 1H); 7.79 (d, J=4.7 Hz, 1H); 7.40 (d, J=16.2 Hz, 1H); 7.26 (d, J=9.0 Hz, 1H); 6.88 (dd, J=7.0 Hz, 1H); 6.77 (d, J=7.9 Hz, 1H); 4.05 (s, 3H); 3.23 (m, 1H); 2.22 (m, 1H); 1.88-1.84 (m, 4H); 1.39 (s, 9H); 1.37-1.24 (m, 4H).

MS (ESI, m/z): 384.0 [M+H]$^+$.

2.iv. trans-{4-[(1R,2R)-1,2-dihydroxy-2-(6-ethoxy-[J, 5]naphthyridin-4-yl)-ethyl]-cyclohexyl}-carbamic acid tert-butyl ester To a mixture of intermediate 2.iii (2.84 g, 7.4 mmol) in 2-methyl-2-propanol (65 ml), EA (15 ml) and water (75 ml) were added at rt, methanesulfonamide (0.85 g) and AD-mix β (12 g). The reaction mixture was stirred for 11 h at rt and sodium bisulfite (14 g) was added portion wise. The two clear layers were decanted and the org. layer was extracted twice with EA (2×100 ml). The combined org. extracts were washed with brine, and concentrated to dryness. The residue was chromatographed (DCM-MeOH 93-7) to afford the title diol (3.0 g, 97% yield) as a white foam.

$^1$H NMR (d6-DMSO) δ: 8.75 (d, J=4.5 Hz, 1H); 8.25 (d, J=9.0 Hz, 1H); 7.74 (d, J=4.5 Hz, 1H); 7.24 (d, J=9.0 Hz, 1H); 6.81 (br s, 1H); 6.68 (d, J=7.9 Hz, 1H); 5.70 (dd, J=1.6, 6.6 Hz, 1H); 5.24 (d, J=6.6 Hz, 1H); 4.17 (d, J=8.0 Hz, 1H); 3.99 (s, 3H); 3.47 (td, J=2.0, 8.0 Hz, 1H); 3.17 (br s, 1H); 2.09-1.96 (m, 2H); 1.84-1.76 (m, 2H); 1.48 (m, 1H); 1.37 (s, 9H); 1.23-0.93 (m, 3H).

MS (ESI, m/z): 418.0 [M+H]$^+$.

2.v. trans-(1R,2R)-1-(4-amino-cyclohexyl)-2-(6-ethoxy-[1,5]naphthyridin-4-yl)-ethane-1,2-diol Starting from intermediate 2.iv (0.6 g, 1.4 mmol), and using the procedure of Example 1, step 1.ix, the title amine (0.32 g, 70% yield) was obtained as a yellowish foam. The compound was purified by chromatography using DCM-MeOH 6-1 containing 1% aq. NH$_4$OH as eluent.

MS (ESI, m/z): 318.2 [M+H]$^+$.

2.vi. 3-oxo-3,4-dihydro-2H-pyrido[3,2-b][1,4]thiazine-6-carboxylic acid trans-{4-[(1R,2R)-1,2-dihydroxy-2-(6-methoxy-[J, 5]naphthyridin-4-yl)-ethyl]-cyclohexyl}-amide To a solution of intermediate 2.v (0.1 g, 0.315 mmol) in DMF (5 ml) were added at rt, 3-oxo-3,4-dihydro-2H-pyrido [3,2-b][1,4]thiazine-6-carboxylic acid (prepared as described in WO 2004/002992, 0.072 g, 1.1 eq), HATU (0.155 g, 1.3 eq.) and DIPEA (0.165 ml, 3.0 eq). The reaction proceeded 2 h and the solvent was removed in vacuo. The residue was taken up in 1M aq. NaOH (2 ml) and water (30 ml). The solids were filtered off, washed with ether. This solid was purified by chromatography (DCM-MeOH 9-1 containing 1% aq. NH$_4$OH) to afford a solid that was further triturated in ether and dried to yield the title compound (0.045 g, 28% yield) as a white solid.

$^1$H NMR (d6-DMSO) δ: 10.96 (s, 1H); 8.76 (d, J=4.5 Hz, 1H); 8.27 (d, J=9.0 Hz, 1H); 7.97-7.92 (m, 2H); 7.76 (d, J=4.5 Hz, 1H); 7.59 (d, J=7.8 Hz, 1H); 7.26 (d, J=9.0 Hz, 1H); 5.73 (m, 1H); 5.28 (m, 1H); 4.24 (m, 1H); 4.02 (s, 3H); 3.73 (m, 1H); 3.65 (s, 2H); 3.52 (m, 1H); 2.15 (m, 1H); 2.03-1.92 (m, 3H); 1.59 (m, 1H); 1.39-1.07 (m, 4H).

MS (ESI, m/z): 510.1 [M+H]$^+$.

Example 3

6-(trans-{4-[(1R,2R)-1,2-dihydroxy-2-(6-methoxy-[1,5]naphthyridin-4-yl)-ethyl]-cyclohexylamino}-methyl)-4H-pyrido[3,2-b][1,4]thiazin-3-one Starting from intermediate 2.v (0.23 g, 0.725 mmol) and 3-oxo-3,4-dihydro-2H-pyrido[3,2-b][1,4]thiazine-6-carbaldehyde (0.154 g, 1.1 eq.) and using the procedure of Example 1, step 1.x, the title compound (0.12 g, 30% yield) was obtained as a white solid. The compound was purified by chromatography using DCM-MeOH 9-1 containing 1% aq. NH$_4$OH as eluent.

$^1$H NMR (d6-DMSO) δ: 10.86 (s, 1H); 8.75 (d, J=4.5 Hz, 1H); 8.26 (d, J=9.0 Hz, 1H); 7.74-7.71 (m, 2H); 7.24 (d, J=9.0 Hz, 1H); 7.10 (d, J=7.8 Hz, 1H); 5.70 (d, J=5.0 Hz, 1H); 5.24 (d, J=6.7 Hz, 1H); 4.16 (d, J=7.8 Hz, 1H); 3.97 (s, 3H); 3.67 (s, 2H); 3.53 (s, 2H); 3.44 (m, 1H); 2.34 (m, 1H); 2.16-1.95 (m, 4H); 1.55 (m, 1H); 1.23-0.84 (m, 5H).

MS (ESI, m/z): 496.2 [M+H$^+$].

Example 4

3-oxo-3,4-dihydro-2H-pyrido[3,2-b][1,4]thiazine-6-carboxylic acid trans-{4-[(1S)-1-hydroxy-2-(6-methoxy-[1,5]naphthyridin-4-yl)-ethyl]-cyclohexyl}-amide

4.i. trans-{4-[(4R,5R)-5-(6-methoxy-[1,5]naphthyridin-4-yl)-2-oxo-[1,3]dioxolan-4-yl]-cyclohexyl}-carbamic acid tert-butyl ester Starting from intermediate 2.iv (2.69 g, 6.44 mmol), and using the procedure of Example 1, step 1.vii, the title cyclic carbonate (1.72 g, 60% yield) was obtained as a colourless foam. The compound was purified by chromatography using Hex-EA 4-1 as eluent.

MS (ESI, m/z): 444.0 [M+H]$^+$.

4.ii. trans-{4-[(1S)-J-hydroxy-2-(6-methoxy-[1,5] naphthyridin-4-yl)-ethyl]-cyclohexyl}-carbamic acid tert-butyl ester Starting from intermediate 4.i (1.72 g, 3.87 mmol) and using the procedure described in Example 1, step 1.viii, the title alcohol (0.3 g, 19% yield) was obtained as a white solid. The compound was purified by chromatography using DCM-MeOH 19-1 as eluent.

MS (ESI, m/z): 402.0 [M+H]$^+$.

4.iii. 1-trans-(4-amino-cyclohexyl)-2-(6-methoxy-[1,5]naphthyridin-4-yl)-ethanol Starting from intermediate 4.ii (0.3 g, 0.747 mmol) and using the procedure of Example 1, step 1.ix, the title amine (0.2 g, 88% yield) was obtained as an off-white solid.

MS (ESI, m/z): 302.2 [M+H]$^+$.

4.iv. 3-oxo-3,4-dihydro-2H-pyrido[3,2-b][1,4]thiazine-6-carboxylic acid trans-{4-[(1S)-1-hydroxy-2-(6-methoxy-[1,5]naphthyridin-4-yl)-ethyl]-cyclohexyl}-amide The title compound (0.055 g, 33% yield) was obtained as a white solid, starting from intermediate 4.iii (0.1 g, 0.332 mmol) and 3-oxo-3,4-dihydro-2H-pyrido[3,2-b][1,4]thiazine-6-carboxylic acid (0.076 g, 1.1 eq), using the procedure of Example 2, step 2.vi. The compound was purified by chromatography using DCM-MeOH 9-1 containing 1% aq. NH$_4$OH as eluent.

$^1$H NMR (d6-DMSO) δ: 10.93 (s, 1H); 8.67 (d, J=4.5 Hz, 1H); 8.25 (d, J=9.0 Hz, 1H); 7.96 (d, J=7.9 Hz, 1H); 7.88 (d, J=7.6 Hz, 1H); 7.59 (d, J=7.9 Hz, 1H); 7.55 (d, J=4.5 Hz, 1H); 7.24 (d, J=9.0 Hz, 1H); 4.52 (d, J=6.2 Hz, 1H); 4.03 (s, 3H); 3.74-3.54 (m, 3H), 3.58 (s, 2H); 2.81 (m, 1H); 2.10-1.86 (m, 4H); 1.35-1.07 (m, 5H).

MS (ESI, m/z): 494.0 [M+H]$^+$.

Example 5

6-(trans-{4-[(1S)-1-hydroxy-2-(6-methoxy-[1,5]naphthyridin-4-yl)-ethyl]-cyclohexylamino}-methyl)-4H-pyrido[3,2-b][1,4]thiazin-3-one Starting from intermediate 4.iii (0.1 g, 0.33 mmol) and 3-oxo-3,4-dihydro-2H-pyrido[3,2-b][1,4]thiazine-6-carbaldehyde (0.070 g, 1.1 eq.) and using the procedure of Example 1, step 1.x, the title compound (0.055 g, 34% yield) was obtained as a white solid. The compound was purified by chromatography using DCM-MeOH 9-1 containing 1% aq. NH$_4$OH as eluent.

$^1$H NMR (d6-DMSO) δ: 10.86 (s, 1H); 8.65 (d, J=4.5 Hz, 1H); 8.24 (d, J=9.0 Hz, 1H); 7.72 (d, J=7.8 Hz, 1H); 7.53 (d, J=4.5 Hz, 1H); 7.23 (d, J=9.0 Hz, 1H); 7.09 (d, J=7.8 Hz, 1H); 4.43 (d, J=6.3 Hz, 1H); 4.00 (s, 3H); 3.73 (s, 2H); 3.72 (m, 1H); 3.53 (m, 1H); 3.52 (s, 2H); 2.78 (dd, J=9.0, 12.6 Hz, 1H); 2.31 (m, 1H); 2.00 (br s, 1H); 1.95 (m, 3H); 1.78 (m, 1H); 1.30-0.93 (m, 5H).

MS (ESI, m/z): 480.3 [M+H]$^+$.

Example 6

6-({trans-4-[(1R,2R)-1,2-dihydroxy-2-(3-methoxy-quinoxalin-5-yl)-ethyl]-cyclohexylamino}-methyl)-4H-pyrido[3,2-b][1,4]thiazin-3-one

6.i. trans-{4-[(E)-2-(3-methoxy-quinoxalin-5-yl)-vinyl]-cyclohexyl}-carbamic acid tert-butyl ester To a solution of 3-methoxy-quinoxaline-5-carbaldehyde (see Preparation B, 1 g, 5.31 mmol) and intermediate 1.iv (2.52 g, 6 mmol) in 1,2-DME (40 ml) cooled to −60° C., was added drop wise over 15 min. KHMDS (0.5M in toluene, 18 ml). The reaction mixture was stirred at −60° C. for 30 min and warmed up to 0° C. over 1 h. Water (100 ml) and EA (200 ml) were added. The aq. layer was extracted twice more (2×200 ml) and the combined org. layers were washed with brine, dried over Na$_2$SO$_4$, and concentrated to dryness. The residue was triturated in water, filtered and washed with ether to afford the title alkene (0.89 g, 39% yield) as an off-white solid. The mother liquor was evaporated to afford impure alkene (1.05 g).

MS (ESI, m/z): 384.1 [M+H]$^+$.

6.ii. {trans-4-[(1R,2R)-1,2-dihydroxy-2-(3-methoxy-quinoxalin-5-yl)-ethyl]-cyclohexyl}-carbamic acid tert-butyl ester Starting from intermediate 6.i (0.89 g, 2.32 mmol), and using the procedure of Example 2, step 2.iv, the title diol (0.585 g, 60% yield) was obtained as a white solid. The compound was purified by chromatography using DCM-MeOH 19-1 as eluent.

$^1$H NMR (d6-DMSO) δ: 8.60 (s, 1H); 7.89-7.85 (m, 2H); 7.63 (t, J=7.8 Hz, 1H); 6.61 (d, J=8.0 Hz, 1H); 5.69 (dd, J=3.0, 6.2 Hz, 1H); 5.12 (d, J=6.2 Hz, 1H); 4.13 (d, J=7.5 Hz, 1H); 4.03 (s, 3H); 3.38 (td, J=3.1, 7.1 Hz, 1H); 3.08 (m, 1H); 2.06 (m, 1H); 1.90-1.77 (m, 3H); 1.37 (s, 9H); 1.29-0.97 (m, 5H).

MS (ESI, m/z): 418.1 [M+H]$^+$.

6.iii. (1R,2R)-1-trans-(4-amino-cyclohexyl)-2-(3-methoxy-quinoxalin-5-yl)-ethane-1,2-diol Starting from intermediate 6.ii (0.58 g, 1.39 mmol), and using the procedure of Example 1, step 1.ix, the title amine (0.345 g, 78% yield) was obtained as a white solid.

$^1$H NMR (d6-DMSO) δ: 8.48 (s, 1H); 7.78-7.73 (m, 2H); 7.51 (t, J=7.8 Hz, 1H); 5.58 (m, 1H); 4.99 (br s, 1H); 4.01 (m, 1H); 3.91 (s, 3H); 3.26 (m, 1H); 2.31 (m, 1H); 1.92 (m, 1H); 1.72-1.63 (m, 3H); 1.33-1.05 (m, 4H); 0.95-0.66 (m, 3H).

MS (ESI, m/z): 318.2 [M+H]$^+$.

6.iv. 6-({trans-4-[(1R,2R)-1,2-dihydroxy-2-(3-methoxy-quinoxalin-5-yl)-ethyl]-cyclohexylamino}-methyl)-4H-pyrido[3,2-b][1,4]thiazin-3-one Starting from intermediate 6.iii (0.1 g, 0.31 mmol) and 3-oxo-3,4-dihydro-2H-pyrido[3,2-b][1,4]thiazine-6-carbaldehyde (0.067 g, 1.1 eq.) and using the procedure of Example 1, step 1.x, the title compound (0.065 g, 42% yield) was obtained as a colourless foam. The compound was purified by chromatography using DCM-MeOH 9-1 containing 1% aq. NH$_4$OH as eluent.

$^1$H NMR (d6-DMSO) δ: 10.84 (s, 1H); 8.60 (s, 1H); 7.89-7.85 (m, 2H); 7.71 (d, J=7.8 Hz, 1H); 7.63 (t, J=7.7 Hz, 1H); 7.08 (d, J=7.8 Hz, 1H); 5.70 (dd, J=3.4, 6.0 Hz, 1H); 5.11 (d, J=6.2 Hz, 1H); 4.12 (d, J=7.3 Hz, 1H); 4.01 (s, 3H); 3.72 (s,

2H); 3.52 (s, 2H); 3.38 (td, J=3.3, 7.2 Hz, 1H); 2.31 (m, 1H); 2.10 (br s, 1H); 2.06 (m, 1H); 1.94-1.84 (m, 2H); 1.38 (m, 1H); 1.30-1.11 (m, 2H); 1.03-0.70 (m, 3H).

MS (ESI, m/z): 496.0 [M+H]$^+$.

Example 7

6-(trans-{4-[(1R,2R)-1,2-dihydroxy-2-(3-methoxy-quinoxalin-5-yl)-ethyl]-cyclohexylamino}-methyl)-4H-pyrido[3,2-b][1,4]oxazin-3-one Starting from intermediate 6.iii (0.1 g, 0.31 mmol) and 3-oxo-3,4-dihydro-2H-pyrido[3,2-b][1,4]oxazine-6-carbaldehyde (0.061 g, 1.1 eq.; prepared as described in WO 2004/014361) and using the procedure of Example 1, step 1.x, the title compound (0.045 g, 29% yield) was obtained as a colourless foam. The compound was purified by chromatography using DCM-MeOH 9-1 1% aq. NH$_4$OH as eluent.

MS (ESI, m/z): 480.0 [M+H]$^+$.

Example 8

6-({trans-4-[(1S,2S)-1,2-dihydroxy-2-(3-methoxy-quinoxalin-5-yl)-ethyl]-cyclohexylamino}-methyl)-4H-pyrido[3,2-b][1,4]thiazin-3-one 8.i. {trans-4-[(1S,2S)-1,2-dihydroxy-2-(3-methoxy-quinoxalin-5-yl)-ethyl]-cyclohexyl}-carbamic acid tert-butyl ester Starting from intermediate 6.i (1.0 g, 2.6 mmol), and using the procedure of Example 2, step 2.iv (with the only exception that AD-mix α was used as a reagent instead of AD-mix β), the title diol (0.54 g, 50% yield) was obtained as a white solid. The compound was purified by chromatography using DCM-MeOH 19-1 as eluent.

MS (ESI, m/z): 418.1 [M+H]$^+$.

8.ii. (1S,2S)-1-trans-(4-amino-cyclohexyl)-2-(3-methoxy-quinoxalin-5-yl)-ethane-1,2-diol Starting from intermediate 8.i (0.54 g, 1.29 mmol), and using the procedure of Example 1, step 1.ix, the title amine (0.29 g, 70% yield) was obtained as a white solid. The compound was purified by chromatography using DCM-MeOH 4-1 1% aq. NH$_4$OH as eluent.

MS (ESI, m/z): 318.2 [M+H]$^+$.

8.iii. 6-({trans-4-[(1S,2S)-1,2-dihydroxy-2-(3-methoxy-quinoxalin-5-yl)-ethyl]-cyclohexylamino}-methyl)-4H-pyrido[3,2-b][1,4]thiazin-3-one Starting from intermediate 8.ii (0.15 g, 0.473 mmol) and 3-oxo-3,4-dihydro-2H-pyrido[3,2-b][1,4]thiazine-6-carbaldehyde (0.101 g, 1.1 eq.) and using the procedure of Example 1, step 1.x, the title compound (0.105 g, 44% yield) was obtained as a colourless foam. The compound was purified by chromatography using DCM-MeOH 9-1 containing 1% aq. NH$_4$OH as eluent.

MS (ESI, m/z): 496.2 [M+H]$^+$.

Example 9

6-(trans-{4-[(1S,2S)-1,2-dihydroxy-2-(3-methoxy-quinoxalin-5-yl)-ethyl]-cyclohexylamino}-methyl)-4H-pyrido[3,2-b][1,4]oxazin-3-one Starting from intermediate 8.ii (0.13 g, 0.41 mmol) and 3-oxo-3,4-dihydro-2H-pyrido[3,2-b][1,4]oxazine-6-carbaldehyde (0.080 g, 1.1 eq.) and using the procedure of Example 1, step 1.x, the title compound (0.054 g, 27% yield) was obtained as a white solid. The compound was purified by chromatography using DCM-MeOH 9-1 containing 1% aq. NH$_4$OH as eluent.

$^1$H NMR (d6-DMSO) δ: 11.14 (s, 1H); 8.60 (s, 1H); 7.89-7.85 (m, 2H); 7.63 (t, J=7.8 Hz, 1H); 7.29 (d, J=8.0 Hz, 1H); 7.00 (d, J=8.0 Hz, 1H); 5.70 (m, 1H); 5.11 (d, J=6.1 Hz, 1H); 4.61 (s, 2H); 4.12 (d, J=7.2 Hz, 1H); 4.01 (s, 3H); 3.69 (s, 2H); 3.42 (m, 1H); 2.40 (m, 1H); 2.04 (m, 1H); 1.94-1.84 (m, 3H); 1.38 (m, 1H); 1.18 (m, 2H); 1.06-0.83 (m, 3H).

MS (ESI, m/z): 480.3 [M+H]$^+$.

Example 10

(1R,2R)-1-{trans-4-[(E)-3-(2,5-difluoro-phenyl)-allylamino]-cyclohexyl}-2-(3-methoxy-quinoxalin-5-yl)-ethane-1,2-diol Starting from intermediate 6.iii (0.1 g, 0.31 mmol) and (E)-3-(2,5-difluoro-phenyl)-propenal (see Preparation C, 0.058 g, 1.1 eq.) and using the procedure of Example 1, step 1.x, the title compound (0.065 g, 43% yield) was obtained as a colourless solid. The compound was purified by chromatography using DCM-MeOH 9-1 containing 1% aq. NH$_4$OH as eluent.

$^1$H NMR (d6-DMSO) δ: 8.60 (s, 1H); 7.89-7.85 (m, 2H); 7.62 (t, J=7.7 Hz, 1H); 7.46 (m, 1H); 7.23 (m, 1H); 7.10 (m, 1H); 6.59 (d, J=16.1 Hz, 1H); 6.50 (dt, J=4.9, 16.1 Hz, 1H); 5.71 (m, 1H); 5.12 (d, J=6.2 Hz, 1H); 4.13 (d, J=7.4 Hz, 1H); 4.02 (s, 3H); 3.41-3.35 (m, 3H); 2.34 (m, 1H); 2.07 (m, 1H); 1.95-1.79 (m, 3H); 1.75 (br s, 1H); 1.40 (m, 1H); 1.28-1.15 (m, 2H); 1.02-0.81 (m, 3H).

MS (ESI, m/z): 469.7 [M+H]$^+$.

Example 11

6-(trans-{4-[(1R)-1-hydroxy-2-(6-methoxy-[1,5]naphthyridin-4-yl)-ethyl]-cyclohexylamino}-methyl)-4H-pyrido[3,2-b][1,4]thiazin-3-one 11.i. trans-{4-[(1S,2S)-1,2-dihydroxy-2-(6-ethoxy-[1,5]naphthyridin-4-yl)-ethyl]-cyclohexyl}-carbamic acid tert-butyl ester To a mixture of intermediate 2.iii (2.20 g, 5.7 mmol)) in 2-methyl-2-propanol (50 ml), EA (11 ml) and water (58 ml) were added at rt, methanesulfonamide (0.85 g) and AD-mix α (9.3 g). The reaction mixture was stirred for 11 h at rt and sodium bisulfite (10.5 g) was added portion wise. The two clear layers were decanted and the org. layer was extracted twice with EA (2×100 ml). The combined org. extracts were washed with brine, and concentrated to dryness to afford the title diol (1.76 g, 73% yield) as a white foam.

$^1$H NMR (d6-DMSO) δ: 8.75 (d, J=4.5 Hz, 1H); 8.25 (d, J=9.0 Hz, 1H); 7.74 (d, J=4.5 Hz, 1H); 7.24 (d, J=9.0 Hz, 1H); 6.81 (br s, 1H); 6.68 (d, J=7.9 Hz, 1H); 5.70 (dd, J=1.6, 6.6 Hz, 1H); 5.24 (d, J=6.6 Hz, 1H); 4.17 (d, J=8.0 Hz, 1H); 3.99

(s, 3H); 3.47 (td, J=2.0, 8.0 Hz, 1H); 3.17 (br s, 1H); 2.09-1.96 (m, 2H); 1.84-1.76 (m, 2H); 1.48 (m, 1H); 1.37 (s, 9H); 1.23-0.93 (m, 3H).
MS (ESI, m/z): 418.0 [M+H]$^+$.

11.ii. trans-{4-[(4S,5S)-5-(6-methoxy-[1,5]naphthy-ridin-4-yl)-2-oxo-[1,3]dioxolan-4-yl]-cyclohexyl}-carbamic acid tert-butyl ester Starting from above diol (1.4 g, 3.35 mmol), and using the procedure of Example 1, step 1.vii, the title cyclic carbonate (1.6 g, quant.) was obtained as a colourless foam.
MS (ESI, m/z): 444.0 [M+H]$^+$.

11.iii. trans-{4-[(1R)-1-hydroxy-2-(6-methoxy-[1,5]naphthyridin-4-yl)-ethyl]-cyclohexyl}-carbamic acid tert-butyl ester Starting from intermediate 11.ii (1.6 g, 3.6 mmol) and using the procedure of Example 1, step 1.viii, the title alcohol (0.38 g, 26% yield) was obtained as a white solid. The compound was purified by chromatography using EA as eluent.
MS (ESI, m/z): 402.0 [M+H]$^+$.

11.iv. 1-(1R)-trans-(4-amino-cyclohexyl)-2-(6-methoxy-[1, 5]naphthyridin-4-yl)-ethanol Starting from intermediate 11.iii (0.38 g, 0.95 mmol) and using the procedure of Example 1, step 1.ix, the title amine (0.8 g, 98% yield) was obtained as an off-white solid.
MS (ESI, m/z): 302.2 [M+H]$^+$.

11v. 6-(trans-{4-[(1R)-J-hydroxy-2-(6-ethoxy-[1,5]naphthyridin-4-yl)-ethyl]-cyclohexylamino}-methyl)-4H-pyrido[3,2-b][1,4]thiazin-3-one Starting from intermediate 11.iii (0.14 g, 0.45 mmol) and 3-oxo-3,4-dihydro-2H-pyrido[3,2-b][1,4]thiazine-6-carbaldehyde (0.090 g, 1.1 eq.) and using the procedure of Example 1, step 1.x, the title compound (0.069 g, 31% yield) was obtained as a white solid. The compound was purified by chromatography using EA-MeOH 9-1 containing 1% aq. NH$_4$OH as eluent.
$^1$H NMR (d6-DMSO) δ: 10.84 (s, 1H); 8.65 (d, J=4.5 Hz, 1H); 8.24 (d, J=9.0 Hz, 1H); 7.72 (d, J=7.8 Hz, 1H); 7.53 (d, J=4.5 Hz, 1H); 7.23 (d, J=9.0 Hz, 1H); 7.09 (d, J=7.8 Hz, 1H); 4.43 (d, J=6.3 Hz, 1H); 4.00 (s, 3H); 3.73 (s, 2H); 3.72 (m, 1H); 3.53 (m, 1H); 3.52 (s, 2H); 2.78 (dd, J=9.0, 12.6 Hz, 1H); 2.31 (m, 1H); 2.00 (br s, 1H); 1.95 (m, 3H); 1.78 (m, 1H); 1.30-0.93 (m, 5H).
MS (ESI, m/z): 480.3 [M+H]$^+$.

Example 12

6-(trans{4-[1-(1R)-hydroxy-2-(6-methoxy-[1,5]naphthyridin-4-yl)-ethyl]-cyclohexylamino}-methyl)-4H-pyrido[3,2-b][1,4]oxazin-3-one Starting from intermediate 11.iii (0.14 g, 0.45 mmol) and 3-oxo-3,4-dihydro-2H-pyrido[3,2-b][1,4]oxazine-6-carbaldehyde (0.083 g, 1.1 eq.) and using the procedure of Example 1, step 1.x, the title compound (0.048 g, 23% yield) was obtained as a white solid. The compound was purified by chromatography using EA-MeOH 9-1 containing 1% aq. NH$_4$OH as eluent.
$^1$H NMR (d6-DMSO) δ: 11.20 (s, 1H); 8.66 (d, J=4.5 Hz, 1H); 8.24 (d, J=9.0 Hz, 1H); 7.54 (d, J=4.4 Hz, 1H); 7.34 (d, J=8.1 Hz, 1H); 7.23 (d, J=9.0 Hz, 1H); 7.05 (d, J=8.1 Hz, 1H); 4.64 (s, sH); 4.46 (d, J=6.3 Hz, 1H); 4.00 (s, 3H); 3.73 (s, 2H); 3.72 (m, 1H); 3.53 (m, 1H); 3.52 (s, 2H); 2.80 (dd, J=9.0, 12.6 Hz, 1H); 2.31 (m, 1H); 2.00 (br s, 1H); 1.95 (m, 3H); 1.78 (m, 1H); 1.30-0.93 (m, 5H).
MS (ESI, m/z): 464.3 [M+H]$^+$.

Example 13

6-(trans-{4-[(1R,2R)-1,2-dihydroxy-2-(6-methoxy-quinolin-4-yl)-ethyl]-cyclohexylamino}-methyl)-4H-pyrido[3,2-b][1,4]thiazin-3-one 13.i. trans-{4-[(E)-2-(6-methoxy-quinolin-5-yl)-vinyl]-cyclohexyl}-carbamic acid tert-butyl ester To a solution of intermediate 1.iv (6.5 g, 15.4 mmol) and 6-methoxy-quinoline-5-carbaldehyde (2.5 g) in 1,2-DME (85 ml) cooled to −35° C., was added drop wise KHMDS (0.5M in THF, 52.4 ml). The reaction was allowed to warm to rt gradually over 2 h 30. Water was added. The mixture was then extracted with EA. The combined organic layers were dried over MgSO$_4$ and concentrated to dryness and the residue crystallized from EA/Hex to afford the title alkene as a white solid (4.1 g, 70% yield).
$^1$H NMR (d6-DMSO) δ: 8.62 (d, J=4.6 Hz, 1H); 7.89 (d, J=9.2 Hz, 1H); 7.52 (d, J=4.6 Hz, 1H); 7.48 (d, J=2.7 Hz, 1H); 7.38 (dd, J=9.2, 2.7 Hz, 1H); 7.18 (d, J=15.6 Hz, 1H); 6.75 (d, J=8.2 Hz, 1H); 6.51 (dd, J=15.6, 7.4 Hz, 1H); 3.90 (s, 3H); 3.28 (m, 1H); 2.25 (m, 1H); 1.9-1.8 (m, 4H); 1.37 (s, 9H); 1.39-1.20 (m, 4H).
MS (ESI, m/z): 382.9 [M+H]$^+$.

13.ii. trans-{4-[(1R,2R)-1,2-dihydroxy-2-(6-methoxy-quinolin-5-yl)-ethyl]-cyclohexyl}-carbamic acid tert-butyl ester To a mixture of intermediate 13.i (2.0 g, 5.2 mmol) in 2-methyl-2-propanol (45 ml), EA (10 ml) and water (52 ml) were added at rt, methanesulfonamide (0.596 g) and AD-mix β (8.5 g). The reaction mixture was stirred for 11 h at rt and sodium bisulfite (9.6 g) was added portion wise. The two clear layers were decanted and the org. layer was extracted twice with EA (2×100 ml). The combined org. extracts were washed with brine, and concentrated to dryness to afford the title diol (0.8 g, 37% yield) as a white foam.
$^1$H NMR (d6-DMSO) δ: 8.70 (d, J=4.5 Hz, 1H); 7.93 (d, J=9.2 Hz, 1H); 7.57 (d, J=4.5 Hz, 1H); 7.39 (dd, J=9.2, 2.7 Hz, 1H); 7.23 (d, J=2.7 Hz, 1H); 6.65 (d, J=8.2 Hz, 1H); 5.35 (s, 2H); 4.39 (d, J=7.5 Hz, 1H); 3.90 (s, 3H); 3.73 (s, 2H); 3.42 (m, 1H); 3.18 (m, 1H); 2.01 (m, 2H); 1.86 (m, 2H); 1.41 (m, 1H); 1.37 (s, 9H); 1.30-1.00 (m, 5H).
MS (ESI, m/z): 417.0 [M+H]$^+$.

13.iii. trans-(1R,2R)-1-(4-amino-cyclohexyl)-2-(6-methoxy-quinolin-4-yl)-ethane-1,2-diol Starting from intermediate 13.ii (0.8 g, 1 mmol), and using the procedure of Example 1, step 1.ix, the title amine (0.32 g, 70% yield) was obtained as a yellowish foam.
MS (ESI, m/z): 318.2 [M+H]$^+$.

13.iv. 6-(trans-{4-[(1R,2R)-1,2-dihydroxy-2-(6-methoxy-quinolin-4-yl)-ethyl]-cyclohexylamino}-methyl)-4H-pyrido[3,2-b][1,4]thiazin-3-one Starting from intermediate 13.iii (0.11 g, 0.35 mmol) and 3-oxo-3,4-dihydro-2H-pyrido[3,2-b][1,4]thiazine-6-carbaldehyde (0.067 g, 1 eq.) and using the procedure of Example 1, step 1.x, the title compound (0.020 g, 11% yield) was obtained as a white solid. The compound was purified by chromatography using EA-MeOH 9-1 containing 1% aq. NH$_4$OH as eluent.

MS (ESI, m/z): 495.2 [M+H]$^+$.

Example 14

6-(trans-{4-[(1R,2R)-1,2-dihydroxy-2-(6-methoxy-quinolin-4-yl)-ethyl]-cyclohexylamino}-methyl)-4H-pyrido[3,2-b][1,4]oxazin-3-one Starting from intermediate 13.iii (0.11 g, 0.35 mmol) and 3-oxo-3,4-dihydro-2H-pyrido[3,2-b][1,4]oxazine-6-carbaldehyde (0.062 g, 1 eq.) and using the procedure of Example 1, step 1.x, the title compound (0.010 g, 6% yield) was obtained as a white solid. The compound was purified by chromatography using EA-MeOH 9-1 containing 1% aq. NH$_4$OH as eluent.

MS (ESI, m/z): 479.2 [M+H]$^+$.

Example 15

6-trans-({4-[(1R)-1-hydroxy-2-(6-methoxy-quinolin-4-yl)-ethyl]-cyclohexylamino}-methyl)-4H-pyrido[3,2-b][1,4]thiazin-3-one

15.i. trans-{4-[(1S,2S)-1,2-dihydroxy-2-(6-methoxy-quinolin-5-yl)-ethyl]-cyclohexyl}-carbamic acid tert-butyl ester To a mixture of intermediate 13.i (2.0 g, 5.2 mmol) in 2-methyl-2-propanol (45 ml), EA (10 ml) and water (52 ml) were added, at rt, methanesulfonamide (0.596 g) and AD-mix a (8.5 g). The reaction mixture was stirred for 11 h at rt and sodium bisulfite (9.6 g) was added portion wise. The two clear layers were decanted and the org. layer was extracted twice with EA (2×100 ml). The combined org. extracts were washed with brine, and concentrated to dryness to afford the title diol (0.8 g, 37% yield) as a white foam.

$^1$H NMR (d6-DMSO) δ: 8.70 (d, J=4.5 Hz, 1H); 7.93 (d, J=9.2 Hz, 1H); 7.57 (d, J=4.5 Hz, 1H); 7.39 (dd, J=9.2, 2.7 Hz, 1H); 7.23 (d, J=2.7 Hz, 1H); 6.65 (d, J=8.2 Hz, 1H); 5.35 (s, 2H); 4.39 (d, J=7.5 Hz, 1H); 3.90 (s, 3H); 3.73 (s, 2H); 3.42 (m, 1H); 3.18 (m, 1H); 2.01 (m, 2H); 1.86 (m, 2H); 1.41 (m, 1H); 1.37 (s, 9H); 1.30-1.00 (m, 5H).

15.ii. trans-{4-[(4S,5S)-5-(6-methoxy-quinolin-4-yl)-2-oxo-[J, 3]dioxolan-4-yl]-cyclohexyl}-carbamic acid tert-butyl ester Starting from intermediate 15 i. (0.800 g, 1.92 mmol), and using the procedure of Example 1, step 1.vii, the title cyclic carbonate (0.9 g, quant.) was obtained as a yellow oil.

$^1$H NMR (d6-DMSO) δ: 8.84 (d, J=4.5 Hz, 1H); 8.05 (d, J=9.2 Hz, 1H); 7.65 (d, J=4.5 Hz, 1H); 7.52 (dd, J=9.2, 2.7 Hz, 1H); 7.37 (d, J=2.7 Hz, 1H); 6.75 (d, J=7.8 Hz, 1H); 6.57 (d, J=5.9 Hz, 1H); 4.79 (t, J=6.0 Hz, 1H); 3.95 (s, 3H); 3.2 (m, 1H); 2.01 (m, 1H); 1.95-1.80 (m, 3H); 1.62 (m, 1H); 1.37 (s, 9H); 1.30-1.00 (m, 4H).

15.iii. trans-{4-[(JR)-J-hydroxy-2-(6-ethoxy-quinolin-4-yl)-ethyl]-cyclohexyl}-carbamic acid tert-butyl ester Starting from intermediate 15.ii (0.840 g, 1.9 mmol) and using the procedure of Example 1, step 1.viii, the title alcohol (0.12 g, 15% yield) was obtained as a white solid. The compound was purified by chromatography using EA as eluent.

$^1$H NMR (d6-DMSO) δ: 8.61 (d, J=4.4 Hz, 1H); 7.91 (d, J=9.2 Hz, 1H); 7.40-7.32 (m, 3H); 6.67 (d, J=7.47 Hz, 1H); 4.56 (d, J=6.1 Hz, 1H); 3.92 (s, 3H); 3.69 (m, 1H); 3.30-3.00 (m, 2H); 2.88 (dd, J=8.8, 13.6 Hz, 1H); 1.95-1.80 (m, 3H); 1.37 (s, 9H); 1.30-1.00 (m, 5H).

15.iv. trans-(1R)-1-(4-amino-cyclohexyl)-2-(6-methoxy-quinolin-4-yl)-ethanol Starting from intermediate 15.iii (0.11 g, 0.28 mmol), and using the procedure of Example 1, step 1.ix, the title amine (0.09 g, 100% yield) was obtained as a yellowish oil.

$^1$H NMR (CDCl$_3$) δ: 8.68 (d, J=4.4 Hz, 1H); 8.04 (d, J=9.2 Hz, 1H); 7.39 (dd, J=2.8, 9.2 Hz, 1H); 7.30-7.25 (m, 2H); 3.96 (s, 3H); 3.82 (m, 1H); 3.38 (m, 1H); 2.98 (m, 1H); 2.70 (m, 1H); 2.10-1.90 (m, 4H); 1.40-1.00 (m, 5H).

15.v. 6-trans-({4-[(JR)-J-hydroxy-2-(6-methoxy-quinolin-4-yl)-ethyl]-cyclohexylamino}-methyl)-4H-pyrido[3,2-b][1,4]thiazin-3-one Starting from intermediate 15.iv (0.085 g, 0.28 mmol) and 3-oxo-3,4-dihydro-2H-pyrido[3,2-b][1,4]thiazine-6-carbaldehyde (0.055 g, 1 eq.) and using the procedure of Example 1, step 1.x, the title compound (0.060 g, 40% yield) was obtained as a white solid. The compound was purified by chromatography using EA-MeOH 9-1 containing 1% aq. NH$_4$OH as eluent.

$^1$H NMR (d6-DMSO) δ: 10.86 (s, 1H); 8.61 (d, J=4.5 Hz, 1H); 7.92 (d, J=9.0 Hz, 1H); 7.72 (d, J=7.8 Hz, 1H); 7.40-7.30 (m, 3H); 7.10 (d, J=7.9 Hz, 1H); 4.54 (d, J=6.1 Hz, 1H); 3.95 (s, 3H); 3.75 (s, 2H); 3.55 (m, 1H); 3.52 (s, 2H); 3.26 (dd, J=3.3, 13.9 Hz, 1H); 2.88 (dd, J=8.9, 13.9 Hz, 1H); 2.31 (m, 1H); 2.10-2.00 (m, 4H); 1.78 (m, 1H); 1.30-0.93 (m, 5H).

MS (ESI, m/z): 479.1 [M+H]$^+$.

Example 16

6-trans-({4-[(1S)-1-hydroxy-2-(6-methoxy-quinolin-4-yl)-ethyl]-cyclohexylamino}-methyl)-4H-pyrido[3,2-b][1,4]thiazin-3-one

16.i. trans-{4-[(4R,5R)-5-(6-methoxy-quinolin-4-yl)-2-oxo-[1,3]dioxolan-4-yl]-cyclohexyl}-carbamic acid tert-butyl ester Starting from intermediate 13.ii (1.58 g, 3.8 mmol), and using the procedure of Example 1, step 11.vii, the title cyclic carbonate (0.1 g, 60% yield) was obtained as a yellow oil.

$^1$H NMR (d6-DMSO) δ: 8.84 (d, J=4.5 Hz, 1H); 8.05 (d, J=9.2 Hz, 1H); 7.65 (d, J=4.5 Hz, 1H); 7.52 (dd, J=9.2, 2.7 Hz, 1H); 7.37 (d, J=2.7 Hz, 1H); 6.75 (d, J=7.8 Hz, 1H); 6.57 (d, J=5.9 Hz, 1H); 4.79 (t, J=6.0 Hz, 1H); 3.95 (s, 3H); 3.20 (m, 1H); 2.01 (m, 1H); 1.95-1.80 (m, 3H); 1.62 (m, 1H); 1.37 (s, 9H); 1.30-1.00 (m, 4H).

16.ii. trans-{4-[(1S)-1-hydroxy-2-(6-methoxy-quinolin-4-yl)-ethyl]-cyclohexyl}-carbamic acid tert-butyl ester 3 g of wet Raney nickel were washed with acetone twice and a solution of intermediate 16.i (1.000 g, 2.26 mmol) in EtOH (20 ml) was added. The mixture was degassed several times and then put under hydrogen atmosphere (1 bar) for 45 min. The catalyst was filtered off and the volatiles were removed under reduced pressure. The title alcohol (0.1 g, 11% yield) was obtained as a white solid. The compound was purified by chromatography using Hex-EA 1-1 and then EA as eluents.

$^1$H NMR (d6-DMSO) δ: 8.61 (d, J=4.4 Hz, 1H); 7.91 (d, J=9.2 Hz, 1H); 7.40-7.32 (m, 3H); 6.67 (d, J=7.47 Hz, 1H); 4.56 (d, J=6.1 Hz, 1H); 3.92 (s, 3H); 3.69 (m, 1H); 3.30-3.00 (m, 2H); 2.88 (dd, J=8.8, 13.6 Hz, 1H); 1.95-1.80 (m, 3H); 1.37 (s, 9H); 1.30-1.00 (m, 5H).

MS (ESI, m/z): 443.1 [M+H]$^+$.

16.iii. trans-(1S)-1-(4-amino-cyclohexyl)-2-(6-methoxy-quinolin-4-yl)-ethanol Starting from intermediate 16.ii (0.1 g, 0.25 mmol), and using the procedure of Example 1, step 1.ix, the title amine (0.075 g, 100% yield) was obtained as a yellowish oil.

MS (ESI, m/z): 301.2 [M+H]$^+$.

16.iv. 6-trans-({4-[(1S)-1-hydroxy-2-(6-methoxy-quinolin-4-yl)-ethyl]-cyclohexylamino}-methyl)-4H-pyrido[3,2-b][1,4]thiazin-3-one Starting from intermediate 16.iii (0.075 g, 0.28 mmol) and 3-oxo-3,4-dihydro-2H-pyrido[3,2-b][1,4]thiazine-6-carbaldehyde (0.049 g, 1 eq.) and using the procedure of Example 1, step 1.x, the title compound (0.083 g, 69% yield) was obtained as a white solid. The compound was purified by chromatography using EA-MeOH 9-1 containing 1% aq. NH$_4$OH as eluent.

$^1$H NMR (d6-DMSO) δ: 10.86 (s, 1H); 8.61 (d, J=4.5 Hz, 1H); 7.92 (d, J=9.0 Hz, 1H); 7.72 (d, J=7.8 Hz, 1H); 7.40-7.30 (m, 3H); 7.10 (d, J=7.9 Hz, 1H); 4.54 (d, J=6.1 Hz, 1H); 3.95 (s, 3H); 3.75 (s, 2H); 3.55 (m, 1H); 3.52 (s, 2H); 3.26 (dd, J=3.3, 13.9 Hz, 1H); 2.88 (dd, J=8.9, 13.9 Hz, 1H); 2.31 (m, 1H); 2.10-2.00 (m, 4H); 1.78 (m, 1H); 1.30-0.93 (m, 5H).

MS (ESI, m/z): 479.2 [M+H]$^+$.

Example 17

(1R,2R)-1-{4-trans-[(E)-3-(2,5-difluoro-phenyl)-allylamino]-cyclohexyl}-2-(6-methoxy-[1,5]naphthyridin-4-yl)-ethane-1,2-diol Starting from intermediate 2.v (0.11 g, 0.34 mmol) and (E)-3-(2,5-difluoro-phenyl)propenal (0.058 g, 1 eq.) and using the procedure of Example 1, step 1.x, the title compound (0.080 g, 49% yield) was obtained as a colourless solid. The compound was purified by chromatography using DCM-MeOH 6-1 containing 1% aq. NH$_4$OH as eluent.

MS (ESI, m/z): 470.0 [M+H]$^+$.

Example 18

(1R,2R)-1-{trans-4-[(E)-3-(2,5-difluoro-phenyl)-allylamino]-cyclohexyl}-2-(8-fluoro-6-methoxy-quinolin-4-yl)-ethane-1,2-diol

18.i. (1R,2R)-1-(trans-4-amino-cyclohexyl)-2-(8-fluoro-6-methoxy-quinolin-4-yl)-ethane-1,2-diol Starting from intermediate 1.iv (1.8 g, 4.27 mmol) and 8-fluoro-6-methoxy-quinoline-4-carbaldehyde (see preparation D, 0.8 g, 3.9 mmol), the title diol (0.68 g, 2 mmol) was obtained as a white solid using successively the procedures of Example 6, step 6.i (Julia coupling, 93% yield), Example 2, step 2.iv. (asymmetric dihydroxylation, 82% yield) and Example 1, step 1.ix. (N-Boc deprotection, 61% yield).

MS (ESI, m/z): 334.9 [M+H]$^+$.

18.ii. (1R,2R)-1-{trans-4-[(E)-3-(2,5-difluoro-phenyl)-allylamino]-cyclohexyl}-2-(8-fluoro-6-methoxy-quinolin-4-yl)-ethane-1,2-diol Starting from intermediate 18.i (0.1 g, 0.3 mmol) and (E)-3-(2,5-difluoro-phenyl)-propenal (0.05 g, 1 eq.) and using the procedure of Example 1, step 1.x, the title compound (0.034 g, 23% yield) was obtained as a white solid. The compound was purified by chromatography using DCM-MeOH 9-1 containing 1% aq. NH$_4$OH as eluent.

MS (ESI, m/z): 487.3 [M+H]$^+$.

Example 19

(E)-3-(2,5-difluoro-phenyl)-N-{trans-4-[(1R,2R)-2-(8-fluoro-6-methoxy-quinolin-4-yl)-1,2-dihydroxy-ethyl]-cyclohexyl}-acrylamide The title compound (0.053 g, 36% yield) was obtained as a white solid, starting from intermediate 18.i (0.1 g, 0.332 mmol) and (E)-3-(2,5-difluoro-phenyl)-acrylic acid (0.055 g, 1 eq) and using the procedure of Example 2, step 2.vi. The compound was purified by chromatography using DCM-MeOH 9-1 containing 1% aq. NH$_4$OH as eluent.

$^1$H NMR (d6-DMSO) δ: 8.75 (d, J=4.5 Hz, 1H); 8.11 (d, J=8.0 Hz, 1H); 7.68 (d, J=4.5 Hz, 1H); 7.50 (m, 1H); 7.42 (d, J=15.8 Hz, 1H); 7.37-7.23 (m, 3H); 7.08 (d, J=2.0 Hz, 1H); 6.72 (d, J=15.8 Hz, 1H); 5.45 (d, J=6.0 Hz, 1H); 5.38 (d, J=6.0 Hz, 1H); 4.42 (d, J=7.5 Hz, 1H); 3.93 (s, 3H); 3.65 (m, 1H); 3.34 (td, J=2.0, 7.5 Hz, 1H); 2.05-1.99 (m, 2H); 1.95-1.87 (m, 2H); 1.55 (m, 1H); 1.38-1.09 (m, 4H).

MS (ESI, m/z): 501.1 [M+H]$^+$.

Example 20

6-({trans-4-[(1R,2R)-2-(8-fluoro-6-methoxy-quinolin-4-yl)-1,2-dihydroxy-ethyl]-cyclohexylamino}-methyl)-4H-pyrido[3,2-b][1,4]thiazin-3-one Starting from intermediate 18.i (0.1 g, 0.3 mmol) and 3-oxo-3,4-dihydro-2H-pyrido[3,2-b][1,4]thiazine-6-carbaldehyde (0.058 g, 1 eq.) and using the procedure of Example 1, step 1.x, the title compound (0.020 g, 11% yield) was obtained as a white solid. The compound was purified by chromatography using DCM-MeOH 9-1 containing 1% aq. NH$_4$OH as eluent.

MS (ESI, m/z): 513.9 [M+H]$^+$.

Example 21

3-(2,5-difluoro-phenyl)-N-{4-[2-(3-fluoro-6-methoxy-[1,5]naphthyridin-4-yl)-1,2-dihydroxy-ethyl]-cyclohexyl}-acrylamide

21.i. (1R,2R)-J-(trans-4-amino-cyclohexyl)-2-(3-fluoro-6-methoxy-[J, 5]naphthyridin-4-yl)-ethane-1,2-diol Starting from intermediate 1.iv (1.77 g, 4.2 mmol) and 3-fluoro-6-methoxy-[1,5]naphthyridine-4-carbaldehyde (see preparation E, 0.824 g, 4 mmol), the title diol (0.56 g, 1.65 mmol) was obtained as a white solid using successively the procedures of Example 6, step 6.i (Julia coupling, 39% yield), Example 2, step 2.iv. (asymmetric dihydroxylation, 99% yield) and Example 1, step 1 ix. (N-Boc deprotection, 99% yield).

MS (ESI, m/z): 336.0 [M+H]$^+$.

21.ii. 3-(2,5-difluoro-phenyl)-N-{4-[2-(3-fluoro-6-methoxy-[J, 5]naphthyridin-4-yl)-1,2-dihydroxy-ethyl]-cyclohexyl}-acylamide The title compound (0.048 g, 32% yield) was obtained as a white solid, starting from intermediate 21.i (0.1 g, 0.332 mmol) and (E)-3-(2,5-difluoro-phenyl)-acrylic acid (0.055 g, 1 eq) and using the procedure of Example 2, step 2.vi. The compound was purified by chromatography using DCM-MeOH 9-1 containing 1% aq. NH$_4$OH as eluent.

MS (ESI, m/z): 502.1 [M+H]$^+$.

Example 22

(1R,2R)-1-{trans-4-[(E)-3-(2,5-difluoro-phenyl)-allylamino]-cyclohexyl}-2-(3-fluoro-6-methoxy-[1,5]naphthyridin-4-yl)-ethane-1,2-diol Starting from intermediate 21.i (0.15 g, 0.44 mmol) and (E)-3-(2,5-difluoro-phenyl)propenal (0.075 g, 1 eq.) and using the procedure of Example 1, step 1.x, the title compound (0.075 g, 34% yield) was obtained as a yellowish foam. The compound was purified by chromatography using DCM-MeOH 9-1 containing 1% aq. NH$_4$OH as eluent.

MS (ESI, m/z): 488.1 [M+H]$^+$.

Example 23

(1R,2R)-1-(3-fluoro-6-methoxy-[1,5]naphthyridin-4-yl)-2-{trans-4-[(E)-3-(3-fluoro-phenyl)-allylamino]-cyclohexyl}-ethane-1,2-diol Starting from intermediate 21.i (0.1 g, 0.30 mmol) and (E)-3-(3-fluoro-phenyl)-propenal (0.044 g, 1 eq.) and using the procedure of Example 1, step 1.x, the title compound (0.050 g, 36% yield) was obtained as a colourless foam. The compound was purified by chromatography using DCM-MeOH 93-7 containing 1% aq. NH$_4$OH as eluent.

MS (ESI, m/z): 470.0 [M+H]$^+$.

Pharmacological Properties of the Invention Compounds

In Vitro Assays

Experimental Methods:

These assays have been performed following the description given in "Methods for dilution Antimicrobial Susceptibility Tests for Bacteria that Grow Aerobically, 4th ed.; Approved standard: NCCLS Document M7-A4; National Committee for Clinical Laboratory Standards Villanova, Pa., USA, 1997". Minimal inhibitory concentrations (MICs; mg/l) were determined in cation-adjusted Mueller-Hinton Broth (BBL) by a microdilution method following NCCLS guidelines (National Committee for Clinical Laboratory Standards. Methods for Dilution Antimicrobial Susceptibility). The pH of the test medium was 7.2-7.3.

Results:

All Example compounds were tested against several Gram positive and Gram negative bacteria.

Typical antibacterial test results are given in the table hereafter (MIC in mg/l).

| Example No. | S. aureus A798 | S. Pneumoniae 49619 | M. catarrhalis A894 |
|---|---|---|---|
| 3 | ≦0.031 | 0.063 | ≦0.031 |
| 10 | ≦0.031 | 0.063 | ≦0.031 |
| 12 | 0.063 | 0.125 | 0.031 |

The invention claimed is:

1. A compound of formula I wherein
R$^1$ represents (C$_1$-C$_4$)alkoxy;
one or two of U, V, W and X represent(s) N, and the remaining represent each independently CH or, in the case of V or X, may also represent CR$^a$;
R$^a$ represents halogen;
R$^2$ represents H or OH;
A represents CH$_2$, CO, CH$_2$CH=CH or COCH=CH;
D represents a phenyl group optionally substituted one or two times by halogen atoms, or D represents a group of the formula in which Q is oxygen or sulfur;
or a salt of said compound.

2. The compound of formula I according to claim 1, wherein R¹ represents methoxy;
or a salt of said compound.

3. The compound of formula I according to claim 1, wherein one or two of U, V, W and X represent(s) N, and the remaining represent each independently CH or, in the case of V or X, may also represent CR$^a$, where R$^a$ represents fluorine;
or a salt of said compound.

4. The compound of formula I according to claim 1, wherein
D is a phenyl group optionally substituted one or two times by halogen atoms;
or a salt of said compound.

5. The compound of formula I according to claim 4, wherein D represents 3-fluorophenyl or 2,5-difluorophenyl;
or a salt of said compound.

6. The compound of formula I according to claim 1, wherein
D is a group of the formula

in which Q is oxygen or sulfur;
or a salt of said compound.

7. The compound of formula I according to claim 1, wherein the compound is:
- -6-({trans-4-[(1R)-1-hydroxy-2-(3-methoxy-quinolin-5-yl)-ethyl]-cyclohexylamino}-methyl)-4H-pyrido[3,2-b][1,4]thiazin-3-one;
- -6-({trans-4-[(1S)-1-hydroxy-2-(3-methoxy-quinolin-5-yl)-ethyl]-cyclohexylamino }-methyl)-4H-pyrido[3,2-b][1,4]thiazin-3-one;
- -3-oxo-3,4-dihydro-2H-pyrido[3,2-b][1,4]thiazine-6-carboxylic acid trans-{4-[(1R,2R)-1,2-dihydroxy-2-(6-methoxy-[1,5]naphthyridin-4-yl)-ethyl]-cyclohexyl}-amide;
- -6-(trans-{4-[(1R,2R)-1,2-dihydroxy-2-(6-methoxy-[1,5]naphthyridin-4-yl)-ethyl]-cyclohexylamino}-methyl)-4H-pyrido[3,2-b][1,4]thiazin-3-one;
- -3-oxo-3,4-dihydro-2H-pyrido[3,2-b][1,4]thiazine-6-carboxylic acid trans-{4-[(1S)-1-hydroxy-2-(6-methoxy-[1,5]naphthyridin-4-yl)-ethyl]-cyclohexyl}-amide;
- -6-(trans-{4-[(1S)-1-hydroxy-2-(6-methoxy-[1,5]naphthyridin-4-yl)-ethyl]-cyclohexylamino}-methyl)-4H-pyrido[3,2-b][1,4]thiazin-3-one;
- -6({trans-4-[(1R,2R)-1,2-dihydroxy-2-(3-methoxy-quinoxalin-5-yl)-ethyl]-cyclohexylamino}-methyl)-4H-pyrido[3,2-b][1,4]thiazin-3-one;
- 6-(trans-{4[(1S,2S)-1,2-dihydroxy-2-(3-methoxy-quinoxalin-5-yl)-ethyl]-cyclohexylamino}-methyl)-4H-pyrido[3,2-b][1,4]oxazin-3-one ;
- -6-({trans-4-[(1S,2S)-1,2-dihydroxy-2-(3-methoxy-quinoxalin-5-yl)-ethyl]-cyclohexylamino}-methyl)-4H-pyrido[3,2-b][1,4]thiazin-3-one;
- -6-(trans-{4-[(1S,2S)-1,2-dihydroxy-2-(3-methoxy-quinoxalin-5-yl)-ethyl]-cyclohexylaminol}-methyl)-4H-pyrido[3,2-b][1,4]oxazin-3-one;
- -(1R,2R)-1-{trans-4-[(E)-3-(2,5-difluoro-phenyl)-allylamino]-cyclohexyl}-2-(3-methoxy -quinoxalin-5-yl)ethane-1,2-diol;
- -6-(trans-{4-[(1R)-1-hydroxy-2-(6-methoxy-[1,5]naphthyridin-4-yl)-ethyl]-cyclohexylamino}-methyl)-4H-pyrido[3,2-b][1,4]thiazin-3-one ;
- -6-(trans  {4-[(1R)-1-hydroxy-2-(6-methoxy-[1,5]naphthyridin-4-yl)-ethyl]-cyclohexylamino }-methyl)-4H-pyrido[3,2-b][1,4]oxazin-3-one;
- -6-(trans-{4-[(1R,2R)-1,2-dihydroxy-2-(6-methoxy-quinolin-4yl)-ethyl]-cyclohexylamino}-methyl)-4H-pyrido[3,2-b][1,4]thiazin-3-one;
- -6-(trans-{4-[(1R,2R)-1,2-dihydroxy-2-(6-methoxy-quinolin-4-yl)-ethyl]-cyclohexylamino}-methyl)-4H-pyrido[3,2-b][1,4]oxazin-3-one;
- -6-trans-({[4-(1R)-1-hydroxy-2-(6-methoxy-quinolin-4-yl)-ethyl]-cyclohexylamino}-methyl)-4H-pyrido[3,2-b][1,4]thiazin-3-one;
- -6-trans-({4-[(1S)-1-hydroxy-2-(6-methoxy-quinolin-4-yl)-ethyl]cyclohexylamino}-methyl)-4H-pyrido[3,2-b][1,4]thiazin-3-one;
- -(1R,2R)-1-{4-trans-[(E)-3-(2,5-difluoro-phenyl)-allylaminol]-cyclohexyl}-2-(6-methoxy -[1,5]naphthyridin-4-yl)-ethane-1,2-diol;
- -(1R,2R)-1-{trans-4-[(E)-3-(2,5-difluoro-phenyl) -allylamino]-cyclohexyl}-2-(8-fluoro -6-methoxy-quinolin-4-yl)-ethane-1,2-diol;
- -(E)-3-(2,5-difluoro-phenyl)-N-{trans-4-[(1R,2R)-2-(8-fluoro-6-methoxy-quinolin-4-yl) -1,2-dihydroxy-ethyl]-cyclohexyl }-acrylamide;
- -6-({trans-4-[(1R,2R)-2-(8-fluoro-6-methoxy-quinolin-4-yl)-1,2-dihydroxy-ethyl]-cyclohexylamino}-methyl)-4H-pyrido[--3,2-b][1,4]thiazin-3-one;
- -3-(2,5-difluoro-phenyl)-N-{4-(3-fluoro-6-methoxy-[1,5]naphthyridin-4-yl) -1,2-dihydroxy-ethyl]-cyclohexyl}-acrylamide;
- -(1R,2R)-1-{ trans-4-[(E)-3-(2,5-difluoro-phenyl)-allylamino]-cyclohexyl}-2-(3-fluoro  -6-methoxy-[1,5] naphthyridin-4-ye-ethane-1,2-diol;
- -(1R,2R)-1-(3-fluoro-6-methoxy-[1,5]naphthyridin-4-yl)-2-{trans-4-[(E)-3-(3-fluoro  -phenyl)-allylamino]-cyclohexyl}-ethane-1,2-diol;
or a salt of said compound.

8. A medicament comprising the compound of formula I as defined in claim 1 or a pharmaceutically acceptable salt of said compound.

9. A pharmaceutical composition comprising, as active principle, the compound of formula I as defined in claim 1 or a pharmaceutically acceptable salt of said compound, and at least one therapeutically inert excipient.

10. A method for treating a bacterial infection comprising administering the compound of formula I as defined in claim 1 to a patient in need thereof, wherein the bacterial infection is caused by *Streptococcus pneumoniae, Haemophilus influenzae, Moraxella catarrhalis, Staphylococcus aureus, Enterococcus faecalis, Enterococcus faecium, Enterococcus casseliflavus, Staphylococcus epidermidis, Streptococcus haemolyticus, Staphylococcus haemolyticus, Peptostreptococcus, Streptococcus pyogenes*, Groups C and G *streptococci, Corynebacterium diphtheriae, Actinobacillus haemolyticum, Mycoplasma pneumoniae, Legionella pneumophila, Chlamydia pneumoniae, Enterococcus durans*, coagulase-negative *staphylococci, Streptococcus agalactiae, Streptococcal* groups C-F, viridans *streptococci, Corynebacterium minutissimum, Clostridium, Bartonella henselae, Enterococcus, Chlamydia trachomatis, Haemophilus ducreyi, Treponema pallidum, Ureaplasma urealyticum, Neiserria gonorrhea*, Groups A, B, and C *streptococci, Helicobacter pylori, Borrelia recurrentis, Borrelia burgdorferi, Chlamydia trachomatis, Listeria, Mycobacterium avium,*

*Mycobacterium intracellulare, Mycobacterium tuberculosis. Mycobacterium leprae, Mycobacterium paratuberculosis, Mycobacterium kansasii, Mycobacterium chelonei, Campylobacter jejuni. Cryptosporidium* spp., *Bordetella pertussis, Clostridium perfringens, or Bacteroide.*

11. The method of claim 10, wherein the bacterial infection is caused by *E. coli, Klebsiella pneumoniae* and other *Enterobacteriaceae, Acinetobacter, Stenothrophomonas maltophilia, Neisseria meningitidis, Bacillus cereus, Bacillus anthracis, Corynebacterium, Propionibacterium acnes,* or *Bacteroide.*

12. The method of claim 10, wherein the bacterial infection is caused by *Staphylococcus aureus.*

13. The method of claim 10, wherein the bacterial infection is caused by *Streptococcus pneumoniae.*

14. The method of claim 10, wherein the bacterial infection is caused by *Moraxella catarrhalis.*

15. A method for treating a protozoal infection comprising administering the compound of formula I as defined in claim 1 to a patient in need thereof, wherein the protozoal infection is caused by *Plasmodium malaria, Plasmodium falciparum, Toxoplasma gondii, Pneumocystis carinii, Trypanosoma brucei,* or *Leishmania.*

* * * * *